(12) United States Patent
Zhu et al.

(10) Patent No.: US 11,484,605 B2
(45) Date of Patent: Nov. 1, 2022

(54) CYSTEINE MODIFIED ANTIBODY-DRUG CONJUGATE AND PREPARATION METHOD THEREOF

(71) Applicant: SICHUAN BAILI PHARMACEUTICAL CO., LTD., Chengdu (CN)

(72) Inventors: Yi Zhu, Chengdu (CN); Yixi Wang, Chengdu (CN); Shi Zhuo, Chengdu (CN); Jie Li, Chengdu (CN); Lan Chen, Chengdu (CN); Weili Wan, Chengdu (CN); Yongguo Yu, Chengdu (CN)

(73) Assignee: BAILI-BIO (CHENGDU) PHARMACEUTICAL CO., LTD., Chengdu (CN)

( * ) Notice: Subject to any disclaimer, the term of this patent is extended or adjusted under 35 U.S.C. 154(b) by 745 days.

(21) Appl. No.: 16/339,719

(22) PCT Filed: Sep. 30, 2017

(86) PCT No.: PCT/CN2017/104706
§ 371 (c)(1),
(2) Date: Apr. 4, 2019

(87) PCT Pub. No.: WO2018/064964
PCT Pub. Date: Apr. 12, 2018

(65) Prior Publication Data
US 2020/0129635 A1 Apr. 30, 2020

(30) Foreign Application Priority Data
Oct. 8, 2016 (CN) .......................... 201610876568.9

(51) Int. Cl.
*A61K 47/68* (2017.01)
*C07K 16/28* (2006.01)

(52) U.S. Cl.
CPC ...... *A61K 47/6817* (2017.08); *C07K 16/2863* (2013.01); *C07K 2317/73* (2013.01); *C07K 2317/92* (2013.01); *C07K 2317/94* (2013.01)

(58) Field of Classification Search
CPC .............................................. A61K 47/68–68
See application file for complete search history.

(56) References Cited

U.S. PATENT DOCUMENTS

| 2010/0215669 A1* | 8/2010 | Chen ........................ A61P 5/14 |
| | | 424/173.1 |
| 2017/0216452 A1 | 8/2017 | Ma et al. |

FOREIGN PATENT DOCUMENTS

| CN | 101065151 A | 10/2007 |
| CN | 102770456 A | 11/2012 |
| CN | 106467575 A | 3/2017 |
| CN | 106866822 A | 6/2017 |
| WO | WO2015157595 A1 | 10/2015 |
| WO | WO2016131769 A2 | 8/2016 |

OTHER PUBLICATIONS

Dimasi et al., Mol. Pharmaceutics 14:1501-16 (Year: 2017).*
IMGTScientificChart, found at imgt.org/IMGTScientificChart/Numbering/Hu_IGHGnbr, updated Jun. 8, 2016, last visited Aug. 9, 2017; IMGT®, the international ImMunoGeneTics information system® http://www.imgt.org (founder and director: Marie-Paule Lefranc, Montpellier, France) (Year: 2017).*
Voynov, V. et al., Design and Application of Antibody Cysteine Variants, Bioconjugate Chem., vol. 21, No. 2, Jan. 21, 2010 (Jan. 21, 2010), pp. 385-392.

* cited by examiner

*Primary Examiner* — Jessica H Roark
(74) *Attorney, Agent, or Firm* — Zhihua Han

(57) ABSTRACT

By inserting cysteine (C) into a heavy chain and/or a light chain of a target antibody at specific insertion site, and performing a site-specific conjugation through a free thiol group (—SH) from the site-specific inserted cysteine and a linker conjugated with a highly potent small molecule cytotoxin, a cysteine modified antibody-drug conjugate with good homogeneity is provided. The specific insertion sites of cysteine are position 205 and/or position 206 (Kabat numbering scheme) of the light chain of the antibody, and/or position 439 (Kabat numbering scheme) of the heavy chain.

7 Claims, 28 Drawing Sheets

Specification includes a Sequence Listing.

A. Antitumor Acitivity of Trop2 ADC as Single Agents in the Treatment of BXPC-3 Human Pancreatic Cancer Xenograft Model

B. The Body Weight Changes of the Mice in the Different Groups

SEQUENCE LISTING

<160> NUMBER OF SEQ ID NOS: 16

<210> SEQ ID NO 1
<211> LENGTH: 990
<212> TYPE: DNA
<213> ORGANISM: Artificial Sequence
<220> FEATURE:
<223> OTHER INFORMATION: Synthesized

<400> SEQUENCE: 1

```
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgcccct ca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                    990
```

<210> SEQ ID NO 2
<211> LENGTH: 330
<212> TYPE: PRT
<213> ORGANISM: Artificial Sequence
<220> FEATURE:
<223> OTHER INFORMATION: Synthesized

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 3
<211> LENGTH: 321
<212> TYPE: DNA
<213> ORGANISM: Artificial Sequence
<220> FEATURE:
<223> OTHER INFORMATION: Synthesized

<400> SEQUENCE: 3
acggtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                                321

<210> SEQ ID NO 4
<211> LENGTH: 106
<212> TYPE: PRT
<213> ORGANISM: Artificial Sequence
<220> FEATURE:
<223> OTHER INFORMATION: Synthesized

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
```

```
              35                  40                  45
Gly Asn Ser Gln Glu Ser Val Thr Glu Gln Asp Ser Lys Asp Ser Thr
         50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 5
<211> LENGTH: 324
<212> TYPE: DNA
<213> ORGANISM: Artificial Sequence
<220> FEATURE:
<223> OTHER INFORMATION: Synthesized

<400> SEQUENCE: 5
acggtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgccctg cgtcacaaag     300
agcttcaaca ggggagagtg ttag                                            324

<210> SEQ ID NO 6
<211> LENGTH: 107
<212> TYPE: PRT
<213> ORGANISM: Artificial Sequence
<220> FEATURE:
<223> OTHER INFORMATION: Synthesized

<400> SEQUENCE: 6

Thr Val Ala Ala Pro Ser Val Phe Ile Phe Pro Pro Ser Asp Glu Gln
  1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
     50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Cys Val Thr Lys Ser Phe Asn Arg Gly Glu Cys
            100                 105

<210> SEQ ID NO 7
<211> LENGTH: 324
<212> TYPE: DNA
<213> ORGANISM: Artificial Sequence
<220> FEATURE:
<223> OTHER INFORMATION: Synthesized

<400> SEQUENCE: 7
acggtggctg caccatctgt cttcatcttc ccgccatctg atgagcagtt gaaatctgga      60
```

```
actgcctctg ttgtgtgcct gctgaataac ttctatccca gagaggccaa agtacagtgg    120
aaggtggata cgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt ctgcacaaag    300
agcttcaaca ggggagagtg ttag                                          324
```

```
<210> SEQ ID NO 8
<211> LENGTH: 107
<212> TYPE: PRT
<213> ORGANISM: Artificial Sequence
<220> FEATURE:
<223> OTHER INFORMATION: Synthesized

<400> SEQUENCE: 8
```

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Cys Thr Lys Ser Phe Asn Arg Gly Glu Cys
            100                 105
```

```
<210> SEQ ID NO 9
<211> LENGTH: 993
<212> TYPE: DNA
<213> ORGANISM: Artificial Sequence
<220> FEATURE:
<223> OTHER INFORMATION: Synthesized

<400> SEQUENCE: 9
```

```
gctagcacca agggcccatc ggtcttcccc ctggcaccct cctccaagag cacctctggg    60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
```

```
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctcctgcct gtctccgggt aaa                                 993
```

<210> SEQ ID NO 10
<211> LENGTH: 331
<212> TYPE: PRT
<213> ORGANISM: Artificial Sequence
<220> FEATURE:
<223> OTHER INFORMATION: Synthesized

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Cys Leu Ser Pro Gly Lys
                325                 330
```

<210> SEQ ID NO 11
<211> LENGTH: 321
<212> TYPE: DNA
<213> ORGANISM: Artificial Sequence
<220> FEATURE:
<223> OTHER INFORMATION: synthesized

<400> SEQUENCE: 11

```
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgccctg cacaaagagc   300
ttcaacaggg gagagtgtta g                                             321
```

<210> SEQ ID NO 12
<211> LENGTH: 106
<212> TYPE: PRT
<213> ORGANISM: Artificial Sequence
<220> FEATURE:
<223> OTHER INFORMATION: synthesized

<400> SEQUENCE: 12

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Cys Thr Lys Ser Phe Asn Arg Gly Glu Cys
            100                 105
```

<210> SEQ ID NO 13
<211> LENGTH: 11
<212> TYPE: PRT
<213> ORGANISM: Artificial Sequence
<220> FEATURE:
<223> OTHER INFORMATION: Synthesized

<400> SEQUENCE: 13

```
Gly Leu Ser Ser Pro Cys Val Thr Lys Ser Phe
1               5                   10
```

<210> SEQ ID NO 14
<211> LENGTH: 11
<212> TYPE: PRT
<213> ORGANISM: Artificial Sequence
<220> FEATURE:
<223> OTHER INFORMATION: Synthesized

<400> SEQUENCE: 14

```
Gly Leu Ser Ser Pro Val Cys Thr Lys Ser Phe
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: Synthesized

<400> SEQUENCE: 15

Thr Gln Lys Ser Leu Ser Cys Leu Ser Pro Gly Lys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthesized

<400> SEQUENCE: 16

Gly Leu Ser Ser Pro Cys Thr Lys Ser Phe
1               5                   10
```

CYSTEINE MODIFIED ANTIBODY-DRUG CONJUGATE AND PREPARATION METHOD THEREOF

CROSS REFERENCE TO RELATED APPLICATION

This application is a national stage application of International application number PCT/CN2017/104706, filed Sep. 30, 2017, which claims the priority benefit of Chinese Patent Application No. 201610876568.9, filed on Oct. 8, 2016, the entire disclosures of which are expressly incorporated by reference herein.

SEQUENCE LISTING

The content of the ASCII text file of the sequence listing named "BACN1901_OA_ST25", which is 16 kb in size was created on and electronically submitted via EFS-Web Nov. 21, 2020, is incorporated herein by reference in its entirety.

TECHNICAL FIELD

The present disclosure relates to therapeutic compounds and methods for the making thereof, and in particular to cysteine modified antibody-cytotoxin conjugates and methods of making thereof.

BACKGROUND

Antibody-drug conjugate (ADC) is a hotspot for targeted therapy. Two drugs, Adcetris and Kadcyla, have been approved for marketing in the United States, and have shown good clinical efficacy. There are more than 50 ADC drugs in Clinical trial stage.

SUMMARY

The present disclosure provides cysteine modified antibody-cytotoxin conjugates (TDC), the methods of making the antibody-cytotoxin conjugates, and methods of using thereof.

In one aspect, the application provides cysteine modified antibody-cytotoxin conjugates. In one embodiment, the cysteine insertion site includes one or more of the following three insertion sites or insertion positions in the target antibodies: light chain position 205 (Kabat numbering scheme, wherein the surrounding amino acid sequence comprises GLSSPCVTKSF (SEQ ID NO:13), with C being the inserted cysteine), light chain 206 (Kabat numbering scheme, wherein the surrounding amino acid sequence comprises GLSSPVCTKSF (SEQ ID NO:14), with C being the inserted cysteine), and heavy chain position 474 (Kabat numbering scheme, wherein the surrounding amino acid sequence comprises TQKSLSCLSPGK (SEQ ID NO:15), with C being the inserted cysteine).

An antibody comprising one or more of the above cysteine insertion mutations retains the ability to bind the antigen as the parental antibody does (affinity). In one embodiment, the present disclosure provides the site-directed coupling of antibody-cytotoxin conjugate (TDC) by a cysteine thiol group with a linker-drug (i.e., linker-cytotoxin), wherein the thiol group is from the cysteine inserted into position 205 or/and position 206 of the light chain or/and position 474 of the heavy chain.

In one embodiment, the application provides cysteine modified antibody-cytotoxin conjugate, comprising an antibody that includes a site-specific inserted cysteine, where cysteine insertion site comprises one or more sites selected from the following three insertion sites: kappa/lambda light chain constant region position 205 (Kabat numbering scheme), kappa/lambda light chain constant region position 206 (Kabat numbering scheme), or the IgG antibody heavy chain constant region position 474 (Kabat numbering scheme).

The amino acid sequence surrounding the cysteine insertion site includes one or more of the following three sequences: LC-205ins:GLSSPCVTKSF (SEQ ID NO:13); LC-206ins: GLSSPVCTKSF (SEQ ID NO:14) or HC-474ins: TQKSLSCLSPGK (SEQ ID NO:15).

In one embodiment, a highly active cytotoxin is conjugated through a linker to a free thiol group from the modified cysteine inserted into specific cysteine insertion sites of the antibody, wherein the antibody light chain comprises amino acid sequence of GLSSPCVTKSF (SEQ ID NO:13) or GLSSPVCTKSF (SEQ ID NO:14), and the antibody heavy chain comprises amino acid sequence of TQKSLSCLSPGK (SEQ ID NO:15), and wherein the C is the cysteine inserted into the light chain position 205, the light chain position 206, or heavy chain position 474 of the antibody.

In one embodiment, the antibody light chain comprises a kappa (κ) or a lambda (λ) isotype. In one embodiment, the antibody heavy chain comprises IgG1, IgG2, IgG3 or IgG4. In one embodiment, the inserted cysteine comprises a thiol group (—SH). In one embodiment, the thiol group (—SH) is capable of chemical conjugation.

In one embodiment, a low molecular weight, high activity cytotoxin is site-specifically linked to the free thiol group of the inserted cysteine via a linker; the low molecular weight, high activity cytotoxin may include, without limitation, MMAE, MMAF, PBD, SN-38, Dox, and their derivatives thereof. The formula of example cytotoxins, MMAE, MMAF, PBD, SN-38, Dox, are shown below:

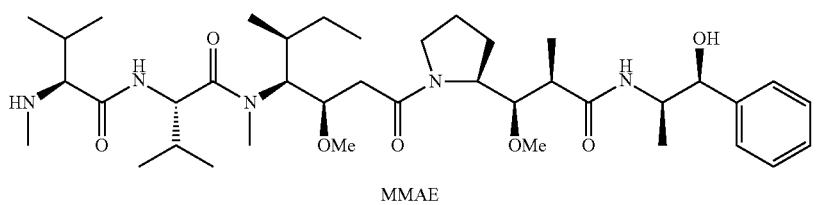

MMAE

-continued

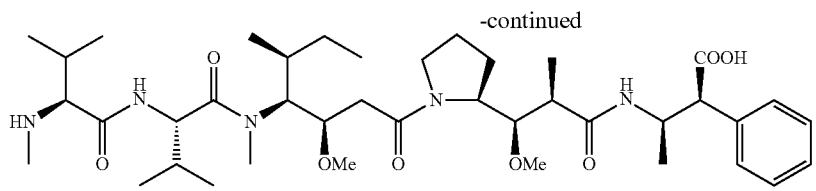

MMAF

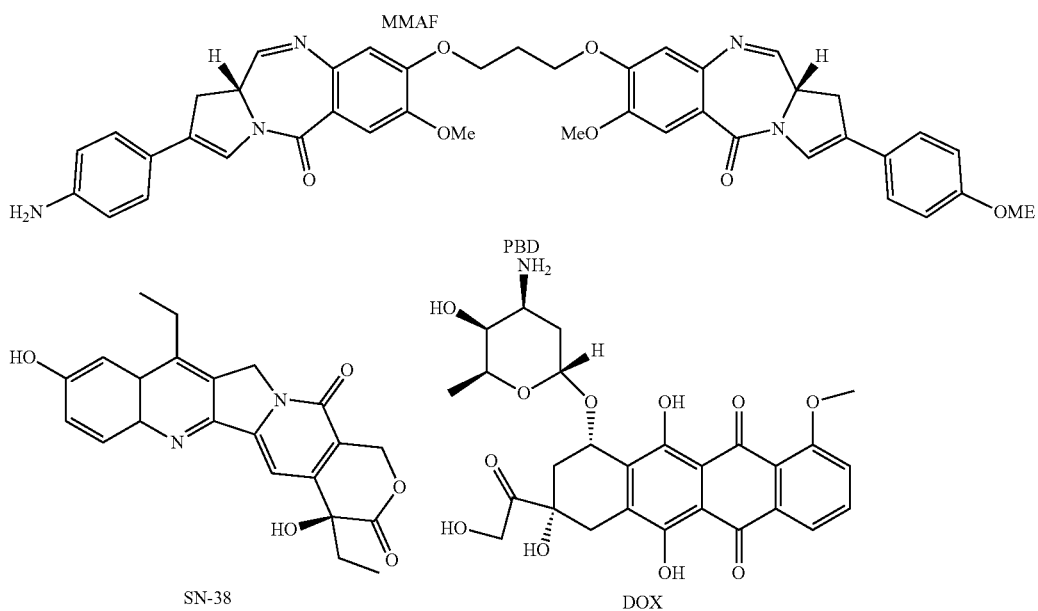

SN-38

DOX

In a further aspect, the application provides methods producing cysteine modified antibody-cytotoxin conjugates. In one embodiment, the method includes the steps of: reducing the antibody with a reducing reagent (such as DTT, TCEP and the like) to provide a reduced antibody, removing the shielding group from the inserted cysteine of the antibody to provide free thiol group; removing the reducing reagent and the removed shielding group by cation exchange chromatography or ultrafiltration; oxidizing the reduced antibody with an oxidant (such as DHAA, $CuSO_4$) to re-connect interchain disulfide bonds of the antibody; adding a linker-drug (i.e., linker-cytotoxin) to conjugate with the free thiol group from the modified cysteine; and removing unconjugated linker-drug by cation exchange chromatography or ultrafiltration.

Amino Acid List:

| Name | Symbol and Abbreviation |
|---|---|
| Alanine | A and Ala |
| Arginine | R and Arg |
| Asparagine | N and Asn |
| Aspartic acid | D and Asp |
| Cysteine | C and Cys |
| Glutamine | Q and Gln |
| Glutamic acid | E and Glu |
| Glycine | G and Gly |
| Histidine | H and His |
| Isoleucine | I and Ile |
| Leucine | L and Leu |
| Lysine | K and Lys |
| Methionine | M and Met |
| Phenylalanine | F and Phe |
| Proline | P and Pro |
| Serine | S and Ser |

-continued

| Name | Symbol and Abbreviation |
|---|---|
| Threonine | T and Thr |
| Tryptophan | W and Trp |
| Tyrosine | Y and Tyr |
| Valine | V and Val |

LC-Cys205insc light chain constant region (Kappa) amino acid sequence
>Cys205ins-Kappa
```
                                            SEQ ID NO: 6
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPCVTKSF

NRGEC
``` wherein, the C in the GLSSPCVTKSF (SEQ ID NO:13) is the site-specific conjugation position. In one embodiment, the cysteine is conjugated with mc-vc-PAB-payload site-specifically.

LC-Cys206insc light chain constant region (Kappa) amino acid sequence
>LC-Cys206ins-Kappa
```
                                            SEQ ID NO: 8
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVCTKSF

NRGEC
``` wherein, the C in the GLSSPVCTKSF (SEQ ID NO:14) is the site-specific conjugation position. In one embodiment, the cysteine is conjugated with mc-vc-PAB-payload site-specifically.

```
IgG1-Fc-Cys439insheavy chain constant region (Fc)
amino acid sequence
>IgG1-Fc-Cys439ins
                                         SEQ ID NO: 10
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKRVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSCLSPGK
``` wherein, the C in the TQKSLSCLSPGK (SEQ ID NO:15) is the site-specific conjugation position. In one embodiment, the cysteine is conjugated with mc-vc-PAB-payload site-specifically.

```
LC-V205C light chain constant region (Kappa) amino
acid sequence
>LC-V205C-Kappa
                                         SEQ ID NO: 12
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPCTKSFN

RGEC
``` wherein, the C in the GLSSPCTKSF (SEQ ID NO:16) is the site-specific conjugation position. In one embodiment, the cysteine is conjugated with mc-vc-PAB-payload site-.

The present disclosure disclosed a novel cysteine modified antibody-cytotoxin conjugate (TDC) that, when compared to non-site-specific conjugated ADC, provides the significant advantages including, without limitation, good homogeneity and low side effect. Preclinical research confirmed that these novel antibody conjugates are significantly superior to non-site-specific conjugated ADC.

The objectives and advantages of the present application will become apparent from the following detailed description of preferred embodiments thereof in connection with the accompanying drawings.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

DETAILED DESCRIPTION OF THE EMBODIMENTS

Figure 1:
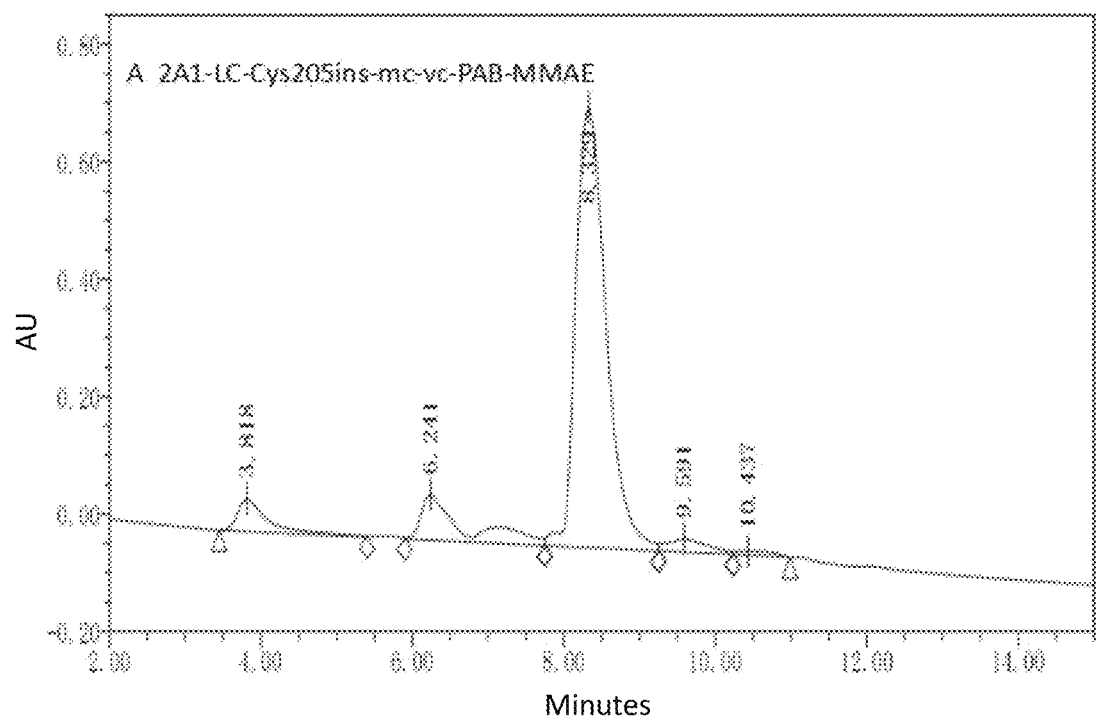
FIG. 1 is an illustration showing the test result of detecting and measuring 2A1-LC-Cys205ins-mc-vc-PAB-MMAE by HIC-HPLC method, as performed in Example 25.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the FIGUREs, can be arranged, substituted, combined, separated, and designed in a wide variety of different configurations, all of which are explicitly contemplated herein.

Example 1: Synthesis and Preparation of mc

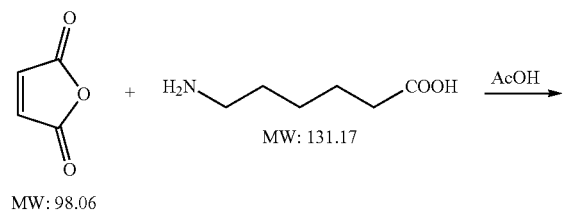

MW: 98.06

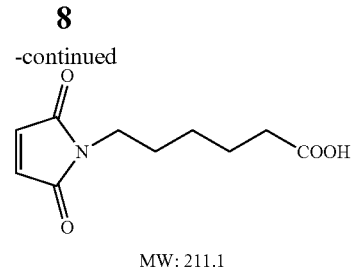

MW: 211.1

6-aminocaproic acid (3.9 g, 0.03 mol) and maleic anhydride (3.5 g, 0.036 mol) were added to glacial acetic acid (30 ml). After stirring at 120° C. for 4-6 h, the reaction was cooled to room temperature. Most of the acetic acid was removed by concentration in vacuum at 60° C. The obtained brownish yellow viscous liquid was poured into water, and then extracted with ethyl acetate (20 ml×3), and the organic layers were combined. The organic layers were washed with water and brine, dried over anhydrous sodium sulfate, filtered and evaporated in vacuo to yield a brown-yellow oil, which was stirred in 50 ml of water, and white solid materials precipitated out of the solution, the white solid materials is filtered, and the product was dried under reduced pressure at 50° C., 5.08 g, yield 80%. Mp: 89-92° C. m/z: 212.2 [M+H]+. 1H NMR (400 Mz, DMSO): 13.21 (br, 1H, COOH), 6.75 (s, 2H, COCH=CHCO), 3.63 (t, 2H, J=7.2 Hz, NCH2CH2), 2.42 (t, 2H, J=7.4 Hz, CH2COOH), 1.52-1.68 (m, 4H, NCH2CH2CH2CH2), 1.30-1.42 (m, 2H, NCH2CH2CH2CH2).

Example 2: Synthesis and Preparation of Mc-OSu

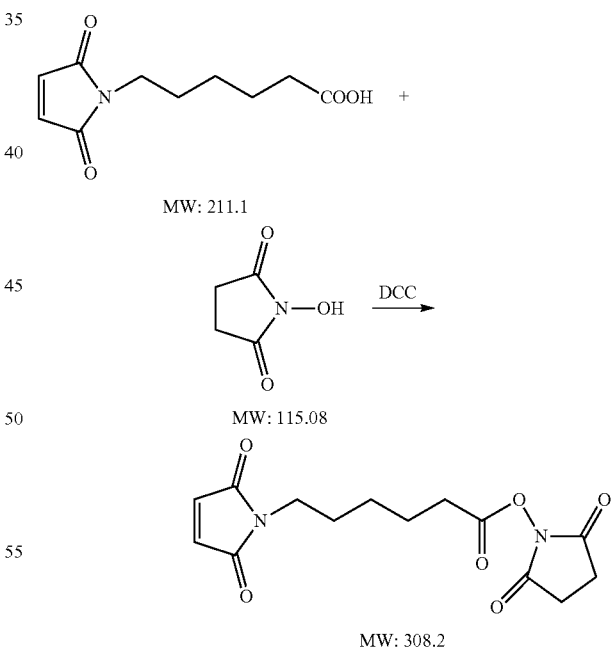

Under nitrogen atmosphere, to a solution of a mixture of MC (4.7 g, 22 mmol) and HOSu (25 g, 22 mmol) in acetonitrile (50 mL) at 0° C. was slowly added DCC (4.5 g, 22 mmol) dissolved in 25 ml acetonitrile. The reaction solution was reacted at 0° C. for 2 hours and then allowed to reacted at room temperature overnight. After filtering, the filter cake was washed with acetonitrile (10 ml×3). The filtrate was concentrated to dry under reduced pressure. The obtained oil was dried under reduced pressure at room temperature for 6 h to afford 6.4 g of pale brown solid, and yield 95%. (To be used directly in the next step without purification) m/z: 309.2 [M+H]+. 1HNMR (400 Mz, CDCl3): 1~2 (m, 6H, CCH2CH2CH2C), 2.68 (t, 2H, CH2CO, 2.95 (s, 4H, COCH2CH2CO), 3.68 (t, 2H, CH2N), 6.81 (s, 2H, CH=CH)

Example 3: Synthesis and Preparation of Fmoc-Val-OSu

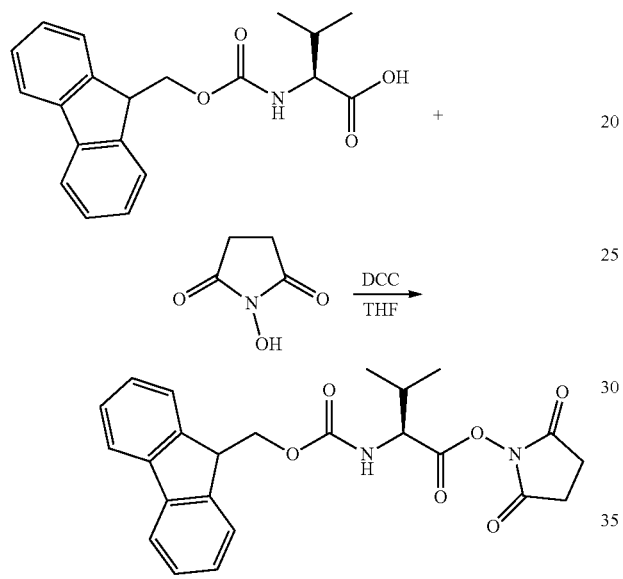

To a solution of a mixture of Fmoc-Val (10 g) and HOSu (3.4 g) in THF (100 mL) at 0° C. was slowly added DCC (6 g) dissolved in 50 ml acetonitrile. The reaction solution was stirred at room temperature for 24 hours. Perform filtration, and the filter cake was washed with THF. A transparent oil was obtained by concentrating the filtrates under reduced pressure. The oil was directly used in the next step directly without further purification. m/z: 474.4 [M+H]+.

Example 4: Synthesis and Preparation of Fmoc-vc

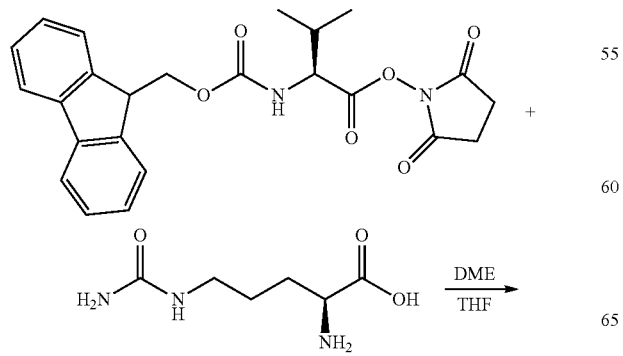

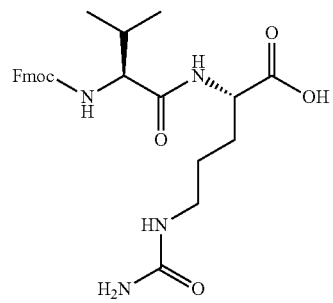

To a solution of Cit (4.0 g) in THF (20 mL) was added a solution of 60 ml aqueous sodium hydrogencarbonate (containing NaHCO$_3$ 2 g, 1.05 eq). A solution of Fmoc-Val-OSu (22.35 mmol) in DME (60 mL) was added to the mixture. After stirred at room temperature for 24 hours, the reaction was added a solution of 15% aqueous citric acid solution (110 ml), and then extracted with EtOAc twice. The combined organic phases were concentrated in vacuum to get a white solid. 100 ml of methyl tert-butyl ether was added to the white material, the mixture was stirred, filtered, and the filter cake was dried under reduced pressure at 40° C. for 4 h to obtain the product 4.83 g, and yield 65%. m/z: 497.6 (M+H)+. 1HNMR (400 Mz, DMSO): 0.92 (6H, m), 1.35~1.65 (4H, m), 2.10 (1H, m), 3.01 (2H, q), 3.99 (1H, t), 4.01-4.45 (2H, m), 4.45 (2H, t), 5.46 (2H, br), 6.03 (1H, t), 7.20-8.02 (8H, m), 8.25 (1H, d).

Example 5: Synthesis and Preparation of Fmoc-vc-PABOH

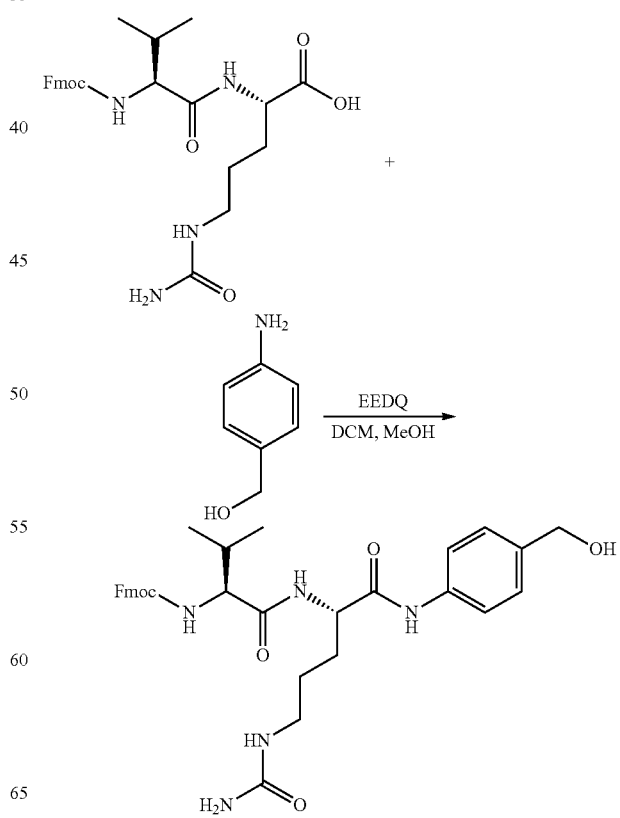

To a solution of Fmoc-vc (2 g, 4.2 mmol) and PABOH (1.04 g, 2 eq) in DCM/MeOH=2/1 (60 mL) was added EEDQ (2.0 g, 2 eq) at 0° C. After stirred for 10 min, a solution of (S)-1-phenylethanamine (17.5 g, 144.2 mmol) in MeOH (200 mL) was added slowly to the mixture after partial dissolution. The reaction system was stirred at room temperature for 2 days in the dark. After completion of the reaction, the mixture was concentrated in vacuum at 40° C. to yield a white solid. The white solid was collected, washed with methyl tert-butyl ether (100 ml), and filtered. The filter cake was washed with methyl tert-butyl ether, and the obtained white solid was dried under reduced pressure at 40° C. to give the white solid 2.2 g, and yield 88%. m/z: 602.6 (M+H)+. $^1$HNMR (400 Mz, DMSO): 0.95 (6H, m), 1.45~1.69 (4H, m), 2.10 (1H, m), 3.11 (2H, m), 3.99 (1H, m), 4.30 (2H, d), 4.05~-4.66 (2H, m), 4.55 (2H, d), 5.21 (1H, t), 5.51 (2H, br), 6.11 (1H, t), 7.09-8.10 (12H, m), 8.21 (1H, d), 10.51 (1H, br).

Example 6: Synthesis and Preparation of vc-PABOH

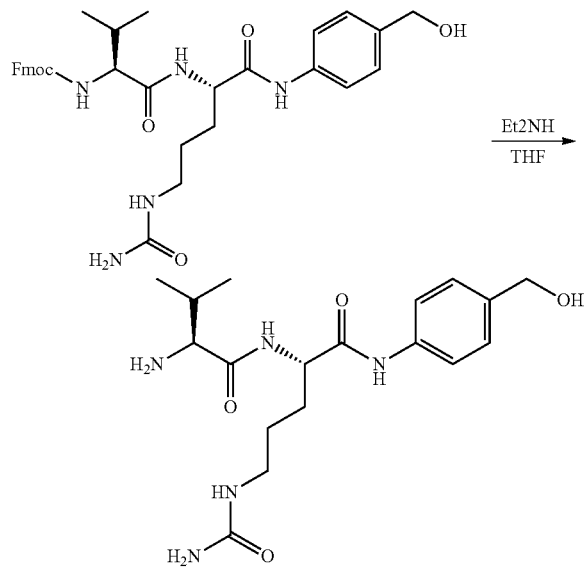

To a solution of Fmoc-vc-PABOH (490 mg, 0.815 mmol) in THF (10 mL) was added diethylamine (2 ml). The reaction mixture was stirred at room temperature for 24 h. 20 ml of DCM was added to the obtained product, the mixture was stirred, and crystalline was precipitated out of reaction solution. Filter the crystalline and the filter cake was washed with DCM, and the obtained solid was dried under reduced pressure to yield 277 mg. The yield was 90%. m/z: 380.2 (M+H)+. 1HNMR (400 Mz, DMSO): 0.89 (6H, m), 1.31~1.61 (4H, m), 1.82 (1H, m), 2.86 (1H, m), 2.89 (2H, d), 4.38 (2H, d), 4.44 (1H, m), 5.01 (1H, br), 5.35 (2H, br), 5.84 (1H, br), 7.14 (2H, d), 7.42 (2H, d), 8.08 (1H, br), 9.88 (1H, br).

Example 7: Synthesis and Preparation of mc-vc-PABOH

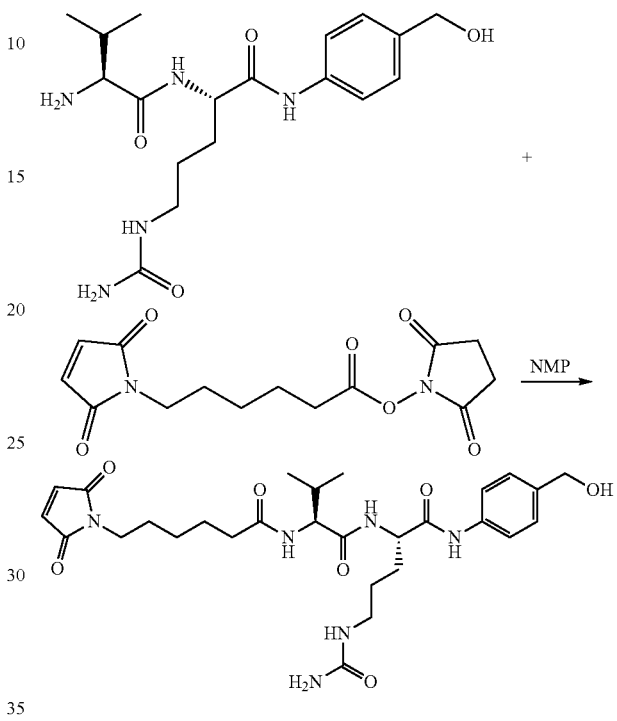

VP-PABOH (205 mg, 0.54 mmol) and MC-OSu (184 mg, 1.1 eq) were added to 10 ml of NMP, and the reaction was stirred at room temperature for 24 h. After completion of the reaction, the mixture was concentrated in vacuo at 40° C. Methyl tert-butyl ether (20 ml) was added to the obtained oil and stirred to crystallization. After filtering the crystalline and washing the filter cake with methyl tert-butyl ether, the product was yielded at 310 mg. The yield is 100%. m/z: 573.3 (M+H)+. 1HNMR (400 Mz, DMSO): 0.89 (6H, m), 1.15-1.99 (10H, m), 2.11 (1H, m), 2.31 (2H, t), 3.21 (2H, m), 3.53 (2H, t), 4.32 (1H, t), 4.51 (1H, m), 4.59 (2H, br), 5.24 (1H, br), 5.56 (2H, br), 6.20 (1H, br), 7.12 (2H, s), 7.23 (2H, d), 7.58 (2H, d), 7.94 (1H, d), 8.17 (1H, d), 10.21 (1H, br)

Example 8: Synthesis and Preparation of mc-vc-PAB-PNP

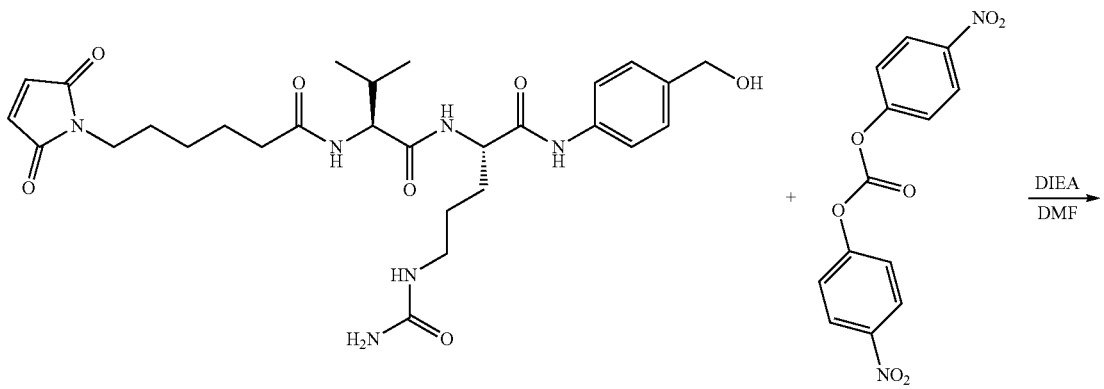

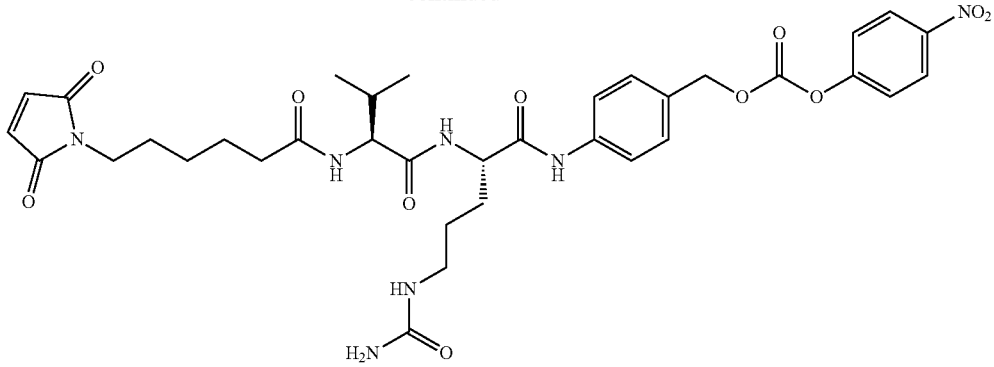

Under nitrogen, to a solution of mc-vc-PABOH (166.0 mg, 0.294 mmol) in anhydrous pyridine (5 ml) was added PNP (179 mg, 3 eq) dissolved in DCM (5 ml) at 0° C. slowly. After stirring at about 0° C. for 10 min, the ice bath was removed, and the reaction was stirred at room temperature for 3 h. After completion of the reaction, EA (70 ml) and a 15% aqueous citric acid solution (100 ml) were added, and the organic layer was separated and recovered. The organic layer was sequentially washed with citric acid, water, brine, dried with anhydrous sodium sulfate, filtered, and the filtrate was concentrated under reduced pressure to yield light yellowish oily product. Adding methyl tert-butyl ether for crystallization resulted in the white-like solid (86 mg). The yield was 40%. m/z: 738 (M+H)+. 1HNMR (400 Mz, CDCl3/CD3OD): 0.84 (6H, m), 1.11-1.84 (10H, m), 2.05 (1H, m), 2.15 (2H, t), 3.09 (2H, m), 3.32 (2H, t), 4.12 (1H, m), 4.38 (1H, m), 5.15 (2H, s), 6.61 (2H, s), 6.84 (1H, d), 7.61 (1H, d), 7.21 (2H, d), 7.50 (2H, d), 7.61 (2H, d), 8.18 (2H, d), 9.59 (1H, br)

Example 9: Synthesis and Preparation of mc-vc-PAB-MMAE

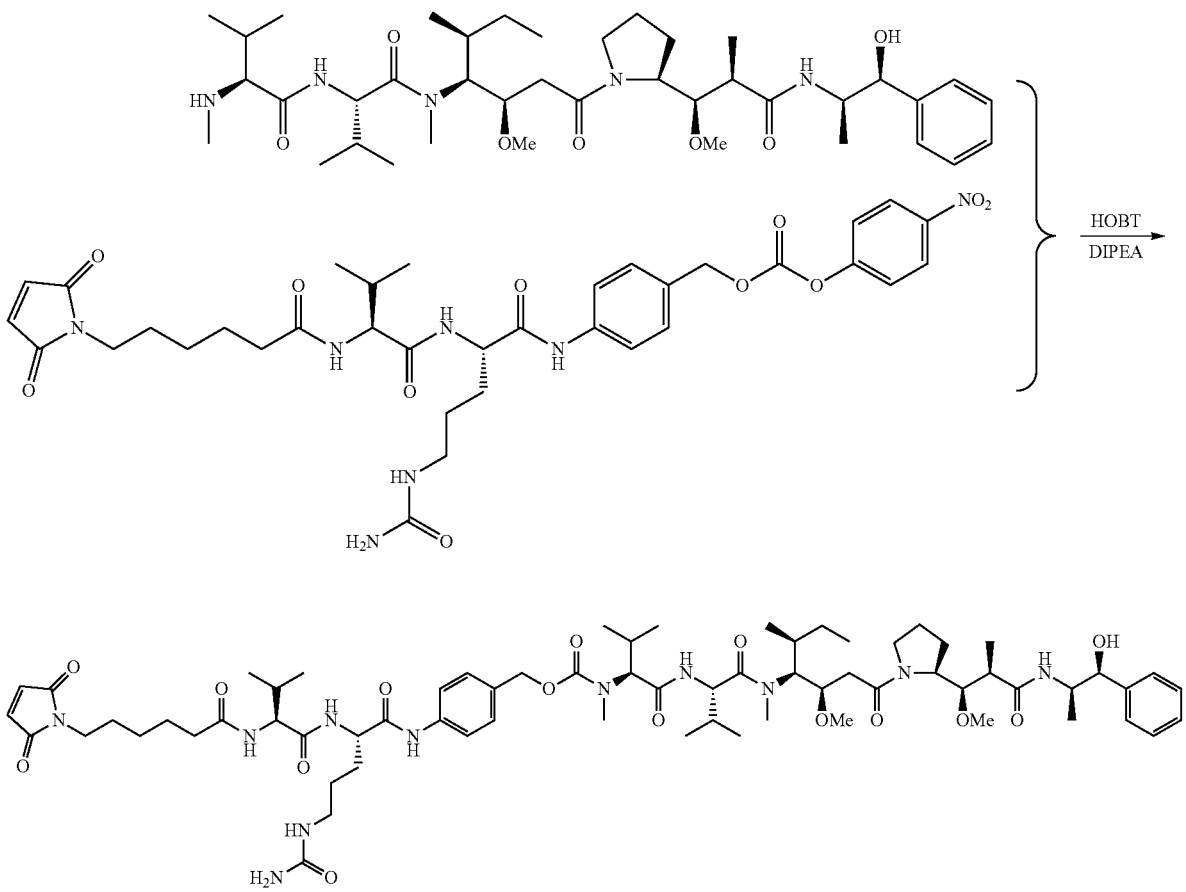

20 mg of mc-vc-PAB-PNP (1.5 eq) and 3 mg of HOBT were added to 2 ml of DMF. After stirring at room temperature for a moment, 13 mg of MMAE, 0.5 ml of pyridine, and 25 ul of DIEA were added. The reaction solution was stirred at room temperature for 2 d. After the reaction is completed, the reaction solution is directly purified by a preparative column, and the desired components are collected, concentrated, and lyophilized to obtain about 10 mg of a product, and the yield is about 42%. m/z: 1317.1 (M+H)+.

Example 10: Synthesis and Preparation of mc-vc-PAB-MMAF

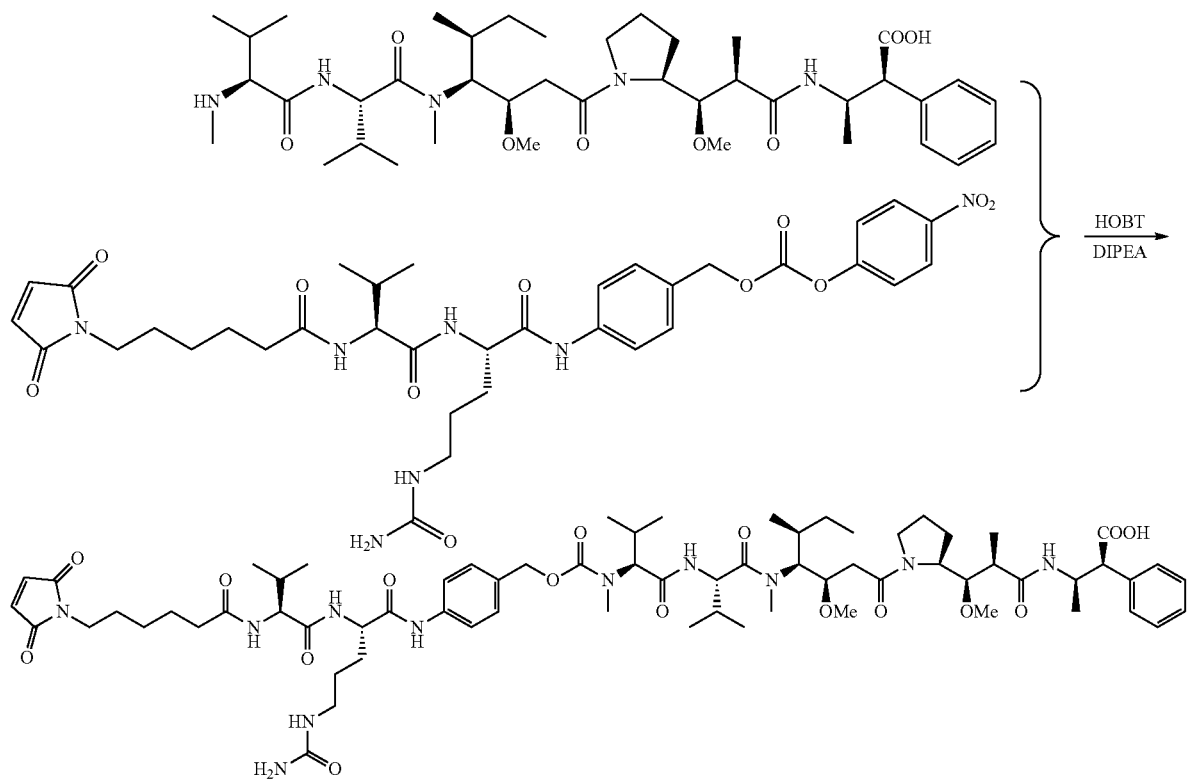

Operate according to the steps of Example 9, about 12.5 mg of mc-vc-PAB-MMAF was obtained, and the yield was 45.2%.

Example 11: Synthesis and Preparation of mc-vc-PAB-PBD

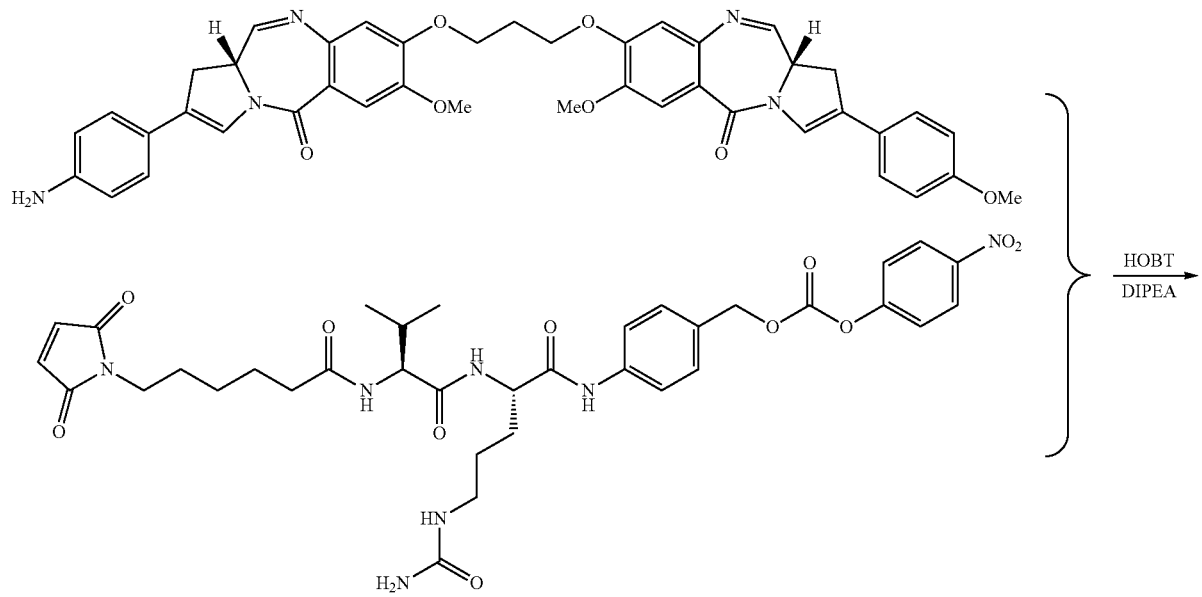

-continued
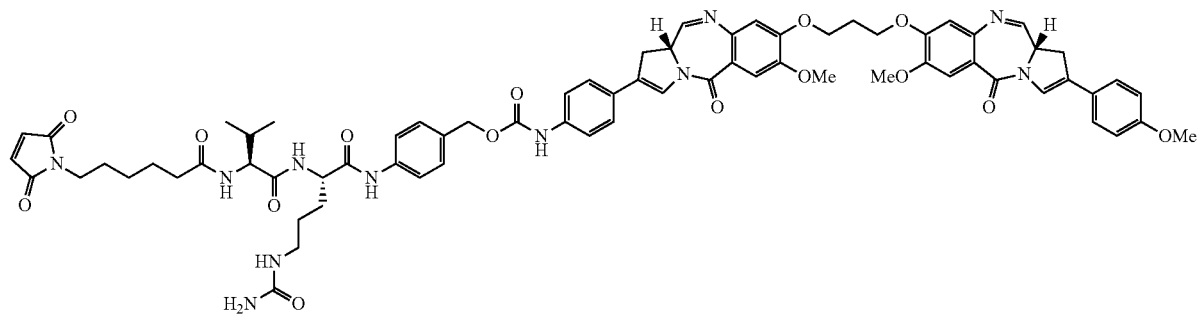
Operate according to the steps of Example 9, about 9.5 mg of mc-vc-PAB-PBD was obtained. The yield was 32.5%. m/z: 1325.4 (M+H)+.
Example 12: Synthesis and Preparation of mc-vc-PAB-DOX
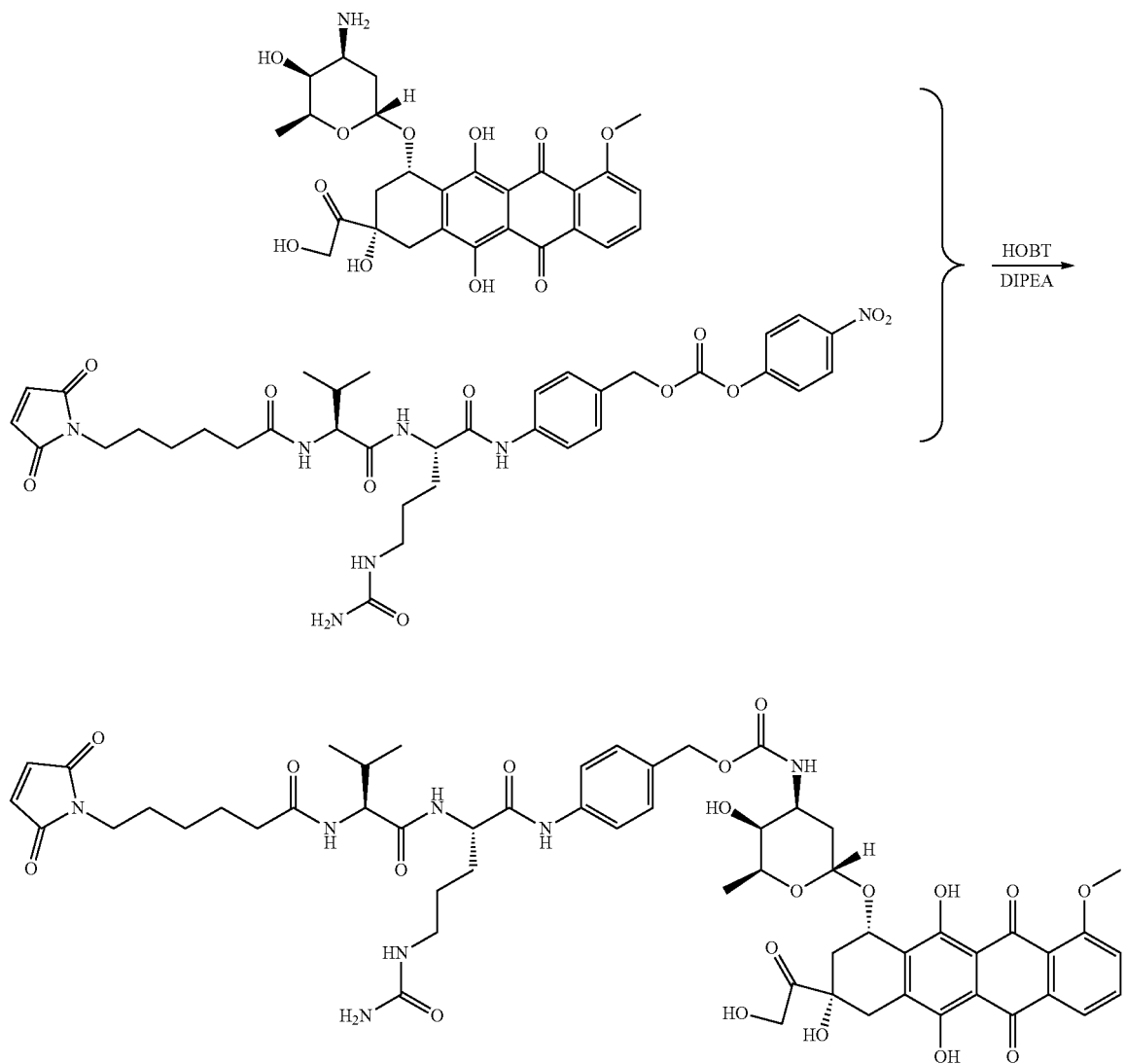

Operate according to the steps of Example 9, about 11.2 mg of mc-vc-PAB-DOX was obtained. The yield was 38.9%. m/z: 1143.2 (M+H)+.

Example 14: Synthesis and Preparation of mc-vc-PAB-SN-38

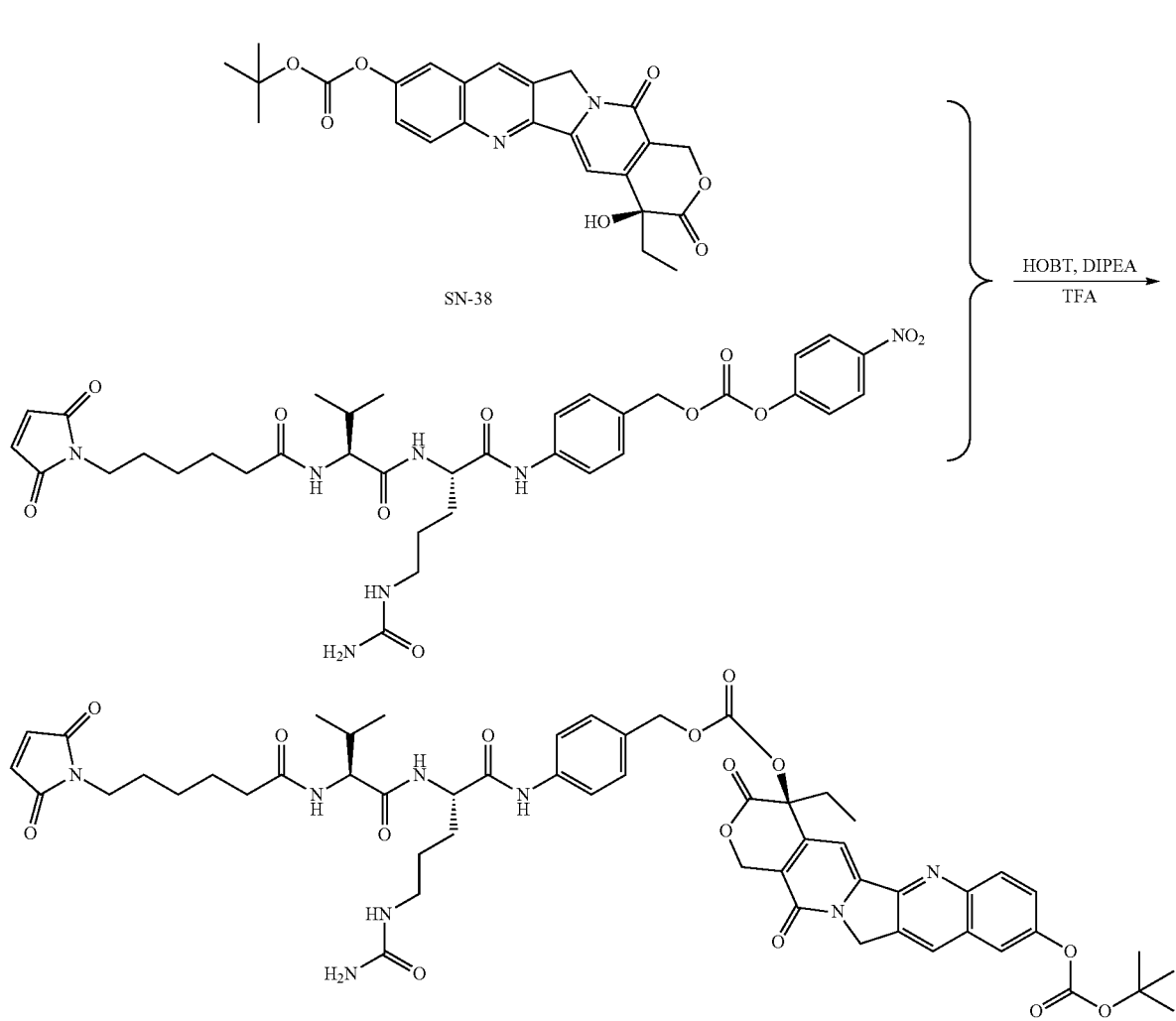

100 mg of 10-O-Boc-SN-38 was dissolved in 10 ml of dry dichloromethane, 25.6 mg (1 eq) of DMAP was added to the solvent, and a solution of triphosgene in dichloromethane was added dropwise at 0° C. (62 mg of triphosgene was dissolved in 2 ml of Dichloromethane), and the reaction was continued at 0° C. for 12 h. The dichloromethane was removed under reduced pressure. The crude products were dissolved in 10 ml of dry DMF, 144 mg of mc-vc-PABOH was then added, and the mixture was stirred at room temperature for 24 h. 41 mg of mc-vc-PAB-SN-38 was isolated by preparation liquid phase separation, and the total yield in two steps was 19.7%. m/z: 1063.2 (M+H)+.

Example 15: Target Antibody Expression and Purification

The target antibody was expressed using Freestyle™ 293-F (Invitrogen) suspension cells. One day before transfection, cells were seeded at a density of $6 \times 10^5$ cells/mL in a 1 L shake flask containing 300 mL of F17 complete medium (Freestyle™ F17 expression medium, Gibco), grew overnight by shaken at 37° C., 5% $CO_2$, 120 rpm at cell incubator. The next day, transfection of the antibody expression plasmid was carried out with PEI, wherein the ratio of plasmid:PEI was 2:1. One day after the transfection, the TN1 feed medium was added at 2.5% (v/v), and the culture was continued for 4 days, and the supernatant was collected by centrifugation.

The collected cell expression supernatant was eluted by a Protein An affinity chromatography column (Mabselect Sure LX, GE) eluting with 0.1 M citric acid (pH 3.0), and the captured antibody was treated with 1 M Tris-HCl (pH 9.0) and adjusted to pH 7.0 at 1/10 (v/v). Remove impurities such as multimers and endotoxin by gel filtration column SEC (Superdex 200, GE), and replace the antibody buffer with PBS (pH 7.4) at the same time, a sample of the target peak of UV280 nm was collected and concentrated to 2 mg/ml through an ultrafiltration centrifuge tube (30 KD, Pall Corporation). The target antibody monomer (PO %) obtained by this method was greater than 90% and was stored for subsequent experiments.

Example 16: Synthesis and Preparation of 2A1-HC-Cys474ins-mc-vc-PAB-MMAE TDC by Conjugating/Coupling 2A1-HC-Cys474ins Antibody and mc-vc-PAB-MMAE The 2A1-HC-Cys474ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 2A1-HC-Cys474ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 2A1-HC-Cys474ins-mc-vc-PAB-MMAE TDC sample.

Example 17: Synthesis and Preparation of 2A1-LC-Cys205ins-mc-vc-PAB-MMAE TDC Sample by Conjugating/Coupling 2A1-LC-Cys205ins Antibody and mc-vc-PAB-MMAE The 2A1-LC-Cys205ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 2A1-LC-Cys205ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 2A1-LC-Cys205ins-mc-vc-PAB-MMAE TDC sample.

Example 18: Synthesis and Preparation of 2A1-LC-Cys206ins-mc-vc-PAB-MMAE TDC Sample by Conjugating/Coupling 2A1-LC-Cys206ins Antibody and mc-vc-PAB-MMAE The 2A1-LC-Cys206ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 2A1-LC-Cys206ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 2A1-LC-Cys206ins-mc-vc-PAB-MMAE TDC sample.

Example 19: Synthesis and Preparation of 4D3-HC-Cys474ins-mc-vc-PAB-MMAE TDC Sample by Conjugating/Coupling 4D3-HC-Cys474ins Antibody and mc-vc-PAB-MMAE The 4D3-HC-Cys474ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 4D3-HC-Cys474ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 4D3-HC-Cys474ins-mc-vc-PAB-MMAE TDC sample.

Example 20: Synthesis and Preparation of 4D3-LC-Cys205ins-mc-vc-PAB-MMAE TDC Sample by Conjugating/Coupling 4D3-LC-Cys205ins Antibody and mc-vc-PAB-MMAE The 4D3-LC-Cys205ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 4D3-LC-Cys205ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 4D3-LC-Cys205ins-mc-vc-PAB-MMAE TDC sample.

Example 21: Synthesis and Preparation of 4D3-LC-Cys206ins-mc-vc-PAB-MMAE TDC Sample by Conjugating/Coupling 4D3-LC-Cys206ins Antibody and mc-vc-PAB-MMAE The 4D3-LC-Cys206ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 4D3-LC-Cys206ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 4D3-LC-Cys206ins-mc-vc-PAB-MMAE TDC sample.

Example 22: Synthesis and Preparation of 4E1-HC-Cys474ins-mc-vc-PAB-MMAE TDC Sample by Conjugating/Coupling 4E1-HC-Cys474ins Antibody and mc-vc-PAB-MMAE The 4E1-HC-Cys474ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 4E1-HC-Cys474ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 4E1-HC-Cys474ins-mc-vc-PAB-MMAE TDC sample.

Example 23: Synthesis and Preparation of 4E1-LC-Cys205ins-mc-vc-PAB-MMAE TDC Sample by Conjugating/Coupling 4E1-LC-Cys205ins Antibody and mc-vc-PAB-MMAE The 4E1-LC-Cys205ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 4E1-LC-Cys205ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 4E1-LC-Cys205ins-mc-vc-PAB-MMAE TDC sample.

Example 24: Synthesis and Preparation of 4E1-LC-Cys206ins-mc-vc-PAB-MMAE TDC Sample by Conjugating/Coupling 4E1-LC-Cys206ins Antibody and mc-vc-PAB-MMAE The 4E1-LC-Cys206ins antibody expressed by the cells was purified by Protein A resin such as Mabselect Sure, eluted with low pH solution and neutralized by adding Tris solution immediately after the low pH elution, and the solution was changed to a pH 7.5 Tris-HCl buffer. The mc-vc-PAB-MMAE compound, being a white powder, was dissolved in DMA for use. In order to remove the masking group on the mutant cysteine residue, the antibody was reduced first. A 1 M aqueous solution of DTT was added to the 4E1-LC-Cys206ins antibody solution at a molecular ratio of 1:40, and the mixture was mixed evenly and reacted at 20° C. for 2 hours. After the reaction time was reached, the pH of the sample was adjusted to 5.0, and the DTT and the masking group in the mixture were removed by cation exchange chromatography such as SP Sepharose F.F. resin. Subsequently, a DHAA solution was added to the sample at a molecular ratio of 1:20 and reacted at 25° C. for 4 hours in the dark to re-connect the interchain disulfide bonds. subsequently, mc-vc-PAB-MMAE solution was added to couple the mc-vc-PAB-MMAE with the inserted or mutant cysteine in the antibody, and the mixture was thoroughly mixed and reacted at 25° C. for 2 hours. After the end of the reaction, mc-vc-PAB-MMAE to which the antibody was not coupled was removed using cation exchange chromatography such as SP Sepharose F.F. to obtain a 4E1-LC-Cys206ins-mc-vc-PAB-MMAE TDC sample.

Figure 2:
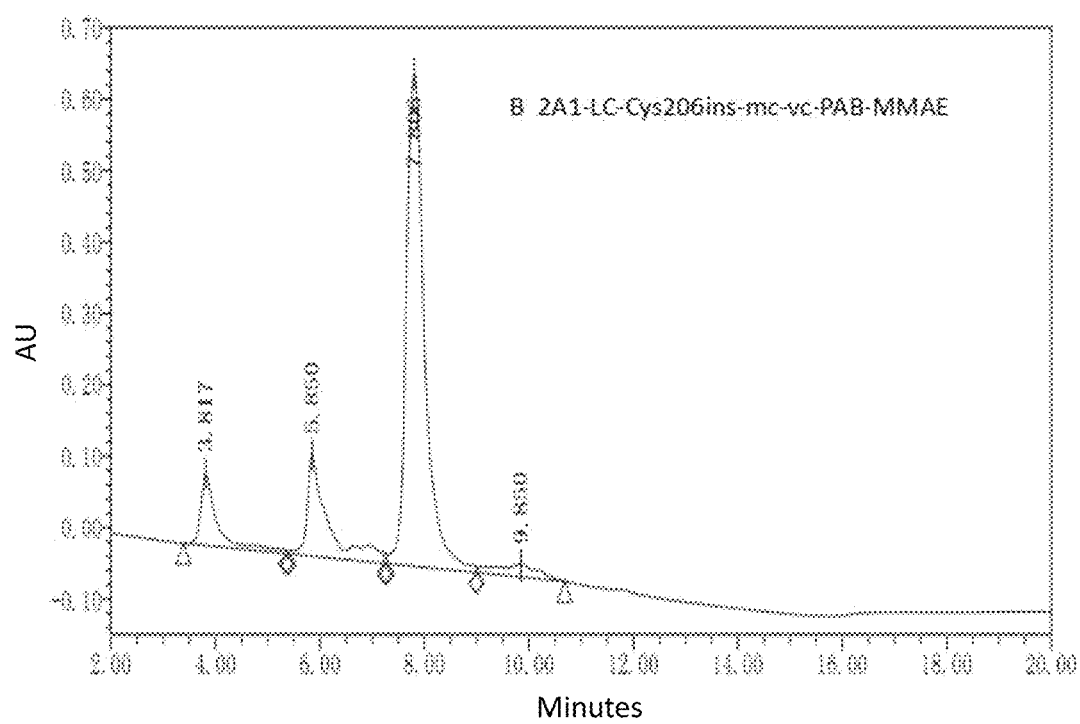
FIG. 2 is an illustration showing the test result of detecting and measuring 2A1-LC-Cys206ins-mc-vc-PAB-MMAE by HIC-HPLC method, as performed in Example 25.
Figure 3:
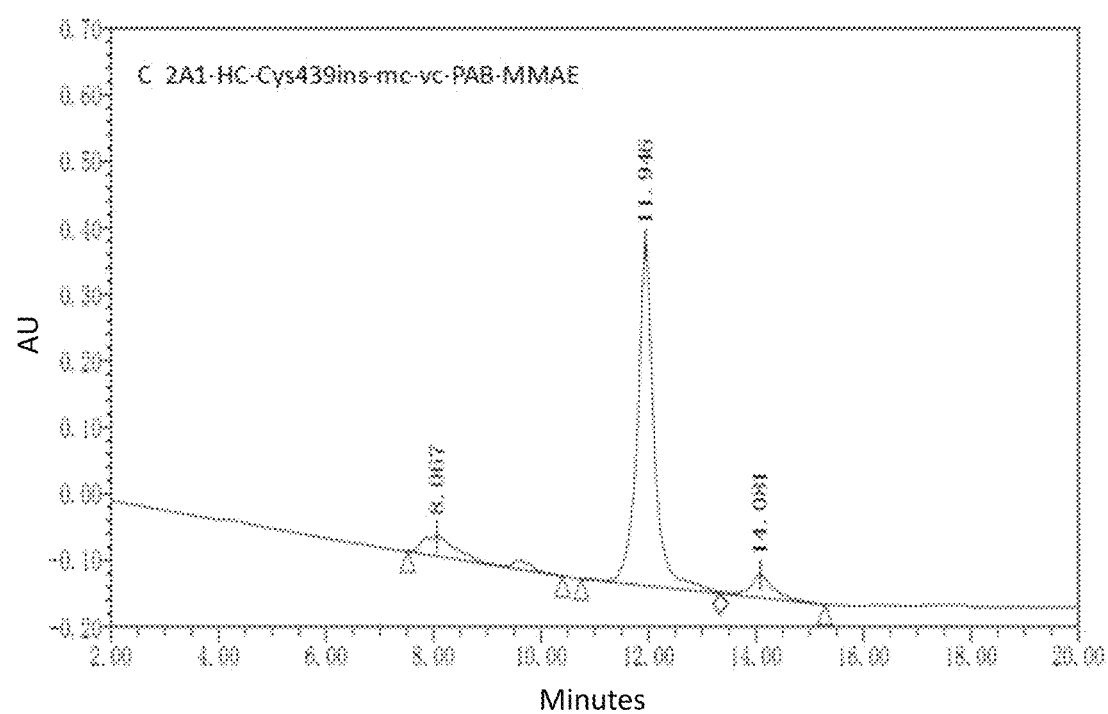
FIG. 3 is an illustration showing the result of detecting and measuring 2A1-HC-Cys474ins-mc-vc-PAB-MMAE by HIC-HPLC method, as performed in Example 25.
Figure 4:
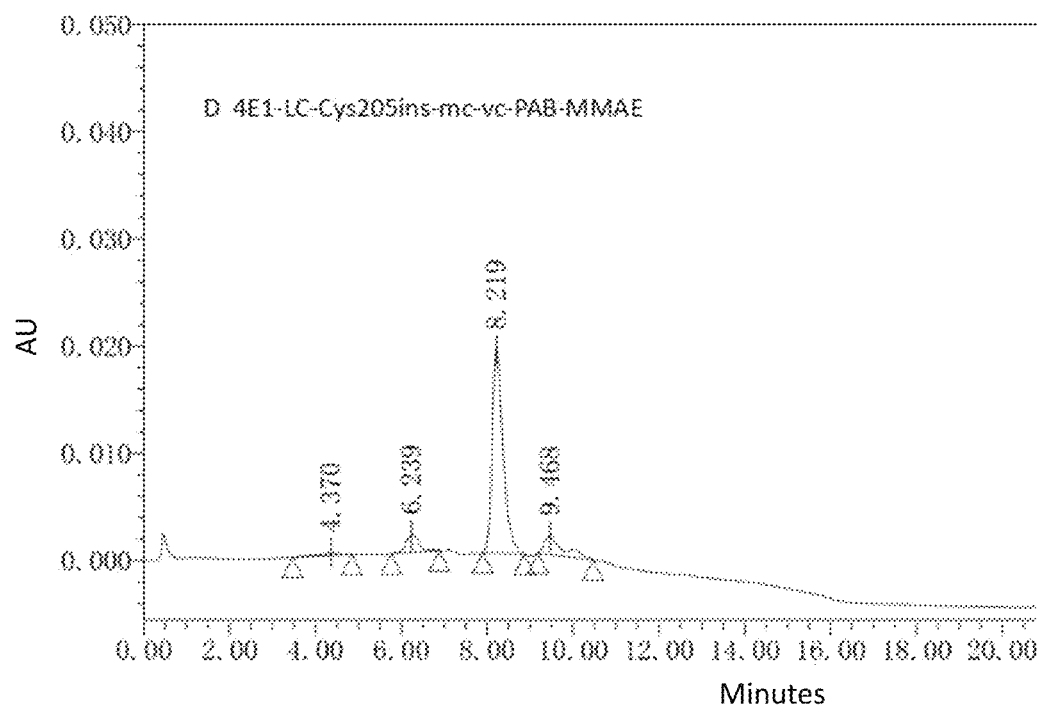
FIG. 4 is an illustration showing the test result of detecting and measuring 4E1-LC-Cys205ins-mc-vc-PAB-MMAE by HIC-HPLC method, as performed in Example 25.
Figure 5:
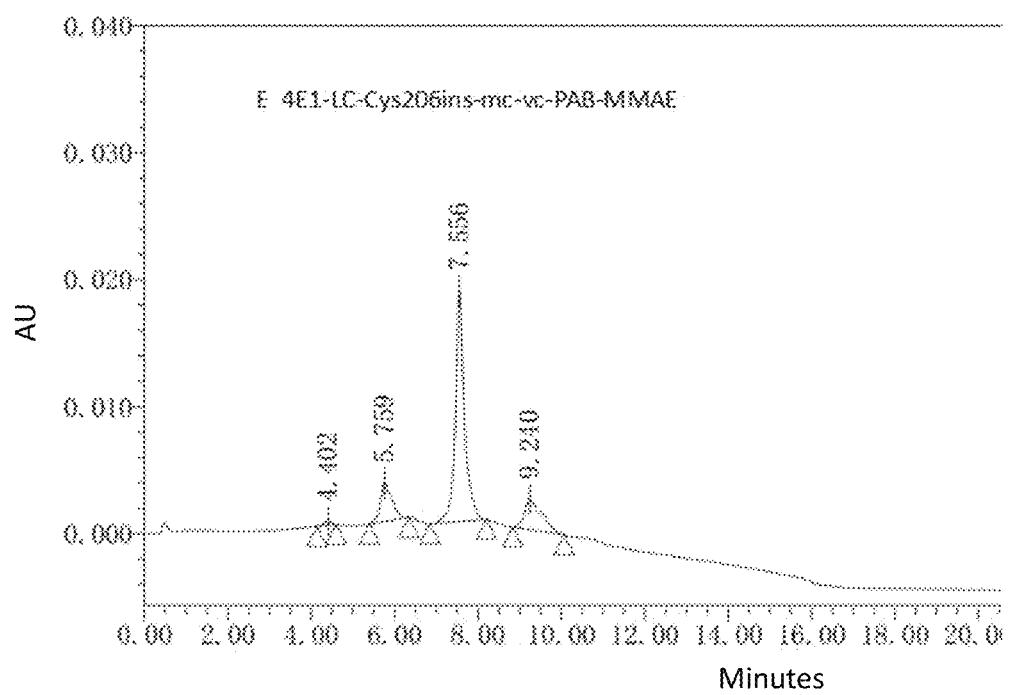
FIG. 5 is an illustration showing the test result of detecting and measuring 4E1-LC-Cys206ins-mc-vc-PAB-MMAE by HIC-HPLC method, as performed in Example 25.
Figure 6:
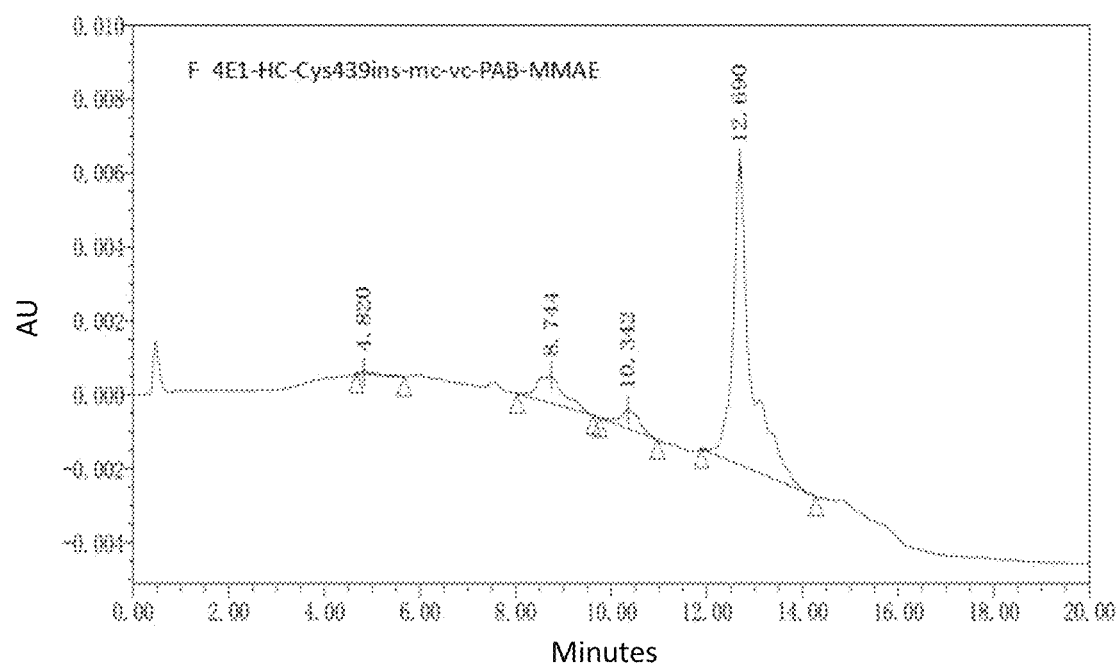
FIG. 6 is an illustration showing the test result of detecting and measuring 4E1-HC-Cys474ins-mc-vc-PAB-MMAE by HIC-HPLC method, as performed in Example 25.
Figure 7:
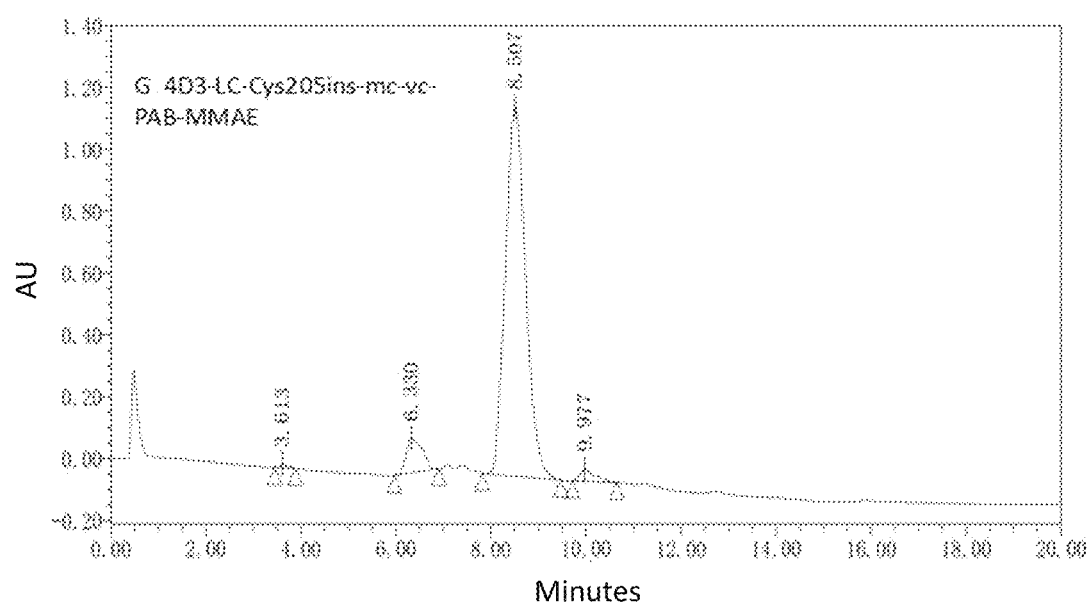
FIG. 7 is an illustration showing the test result of detecting and measuring 4D3-LC-Cys205ins-mc-vc-PAB-MMAE by HIC-HPLC method, as performed in Example 25.
Figure 8:
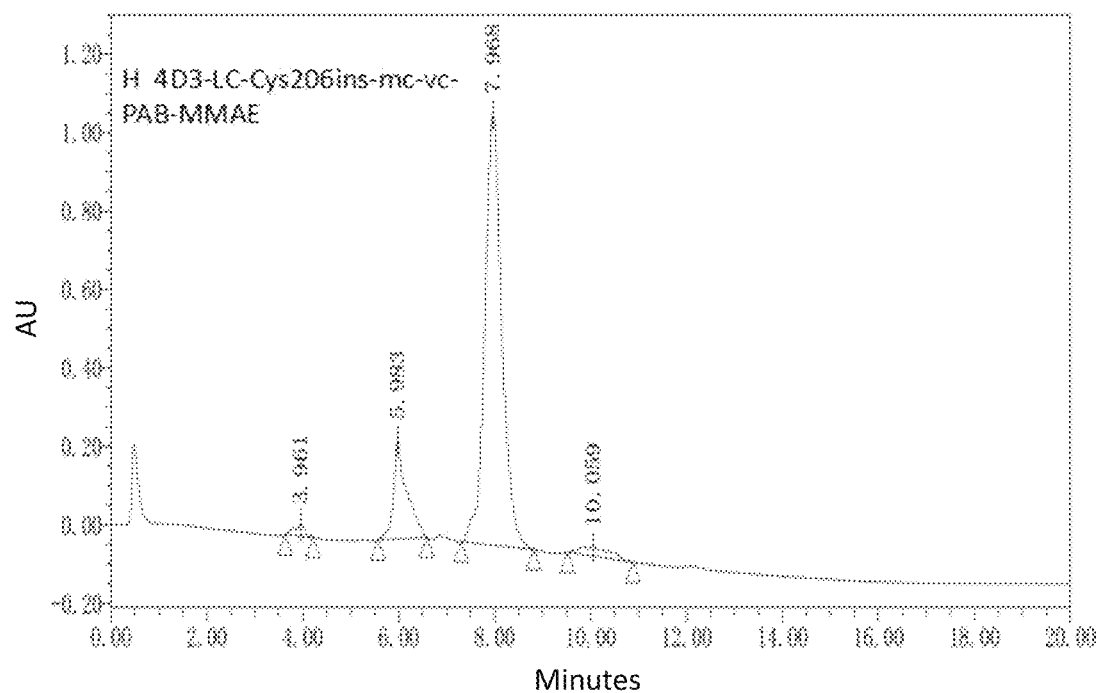
FIG. 8 is an illustration showing the result of detecting and measuring 4D3-LC-Cys206ins-mc-vc-PAB-MMAE by HIC-HPLC method, as performed in Example 25.

Example 25: Measurement of Toxin:Antibody Ratio (DAR, Drug Antibody Ratio) by HIC-HPLC The TDC sample was analyzed by high performance liquid chromatography with hydrophobic chromatography, and drug:antibody ratio (DAR, also known as toxin:antibody ratio) was calculated from the corresponding peak area. One specific method is described in detail as follows:
Column: Proteomix® HICBu-NP5 (5 μm, 4.6×35 mm);
Mobile phase: Buffer A: 2M ammonium sulfate, 0.025 M, pH 7 phosphate buffer; Buffer B: 0.025 M, pH 7 phosphate buffer; Buffer C: 100% isopropanol;
Buffer A was used for equilibration, Buffer B and buffer C were used for gradient elution, detection was performed at 25° C., 214 nm and 280 wavelengths. Based on data gathered from FIGS. 1-3, the site-specific coupled DAR is calculated to be between 1.6 and 1.7, showing excellent compound uniformity or homogeneity. Based on data gathered from FIGS. 4-6, the site-specific coupled DAR is calculated to be between 1.6 and 1.95, showing excellent compound uniformity or homogeneity. Based on data gathered from FIGS. 7-8, the site-specific coupled DAR is calculated to be between 1.6 and 1.9, showing excellent compound uniformity or homogeneity.

Figure 9:
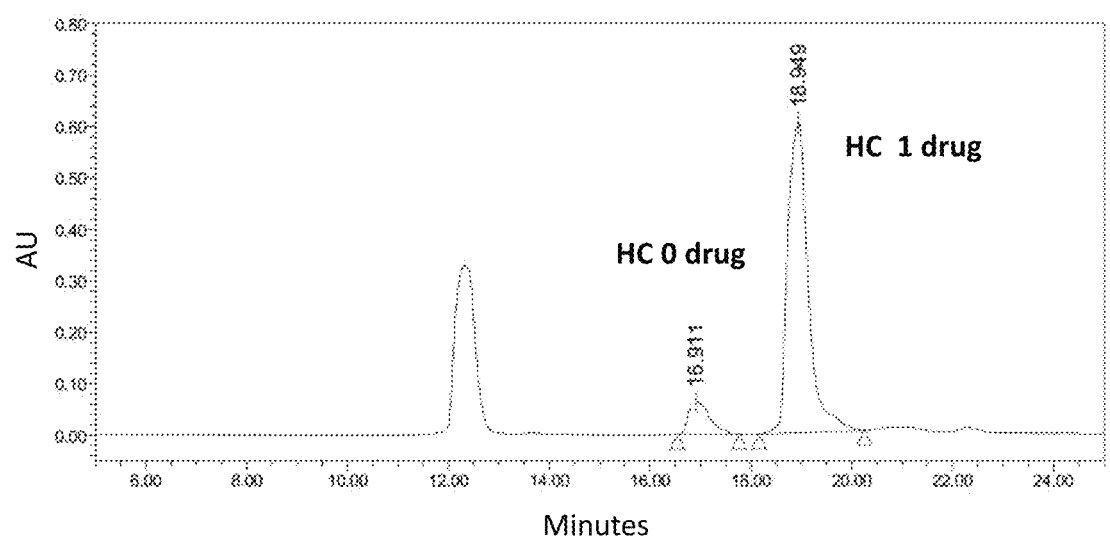
FIG. 9 is an illustration showing the test result of detecting and measuring toxin/antibody ratio of 4D3-HC-Cys474ins-mc-vc-PAB-MMAE by RP-HPLC method, as performed in Example 26.
Figure 10:
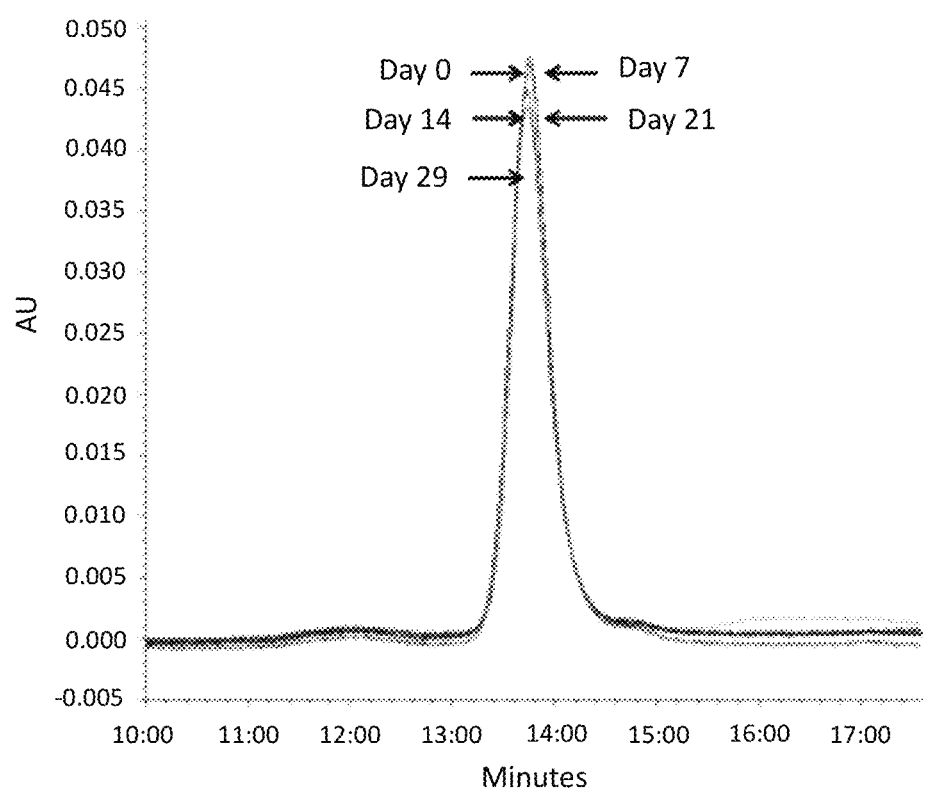
FIG. 10 is an illustration showing the test result of detecting and measuring TDC antibody skeleton 4D3 aggregation by SEC-HPLC method, as performed in Example 27.
Figure 11:
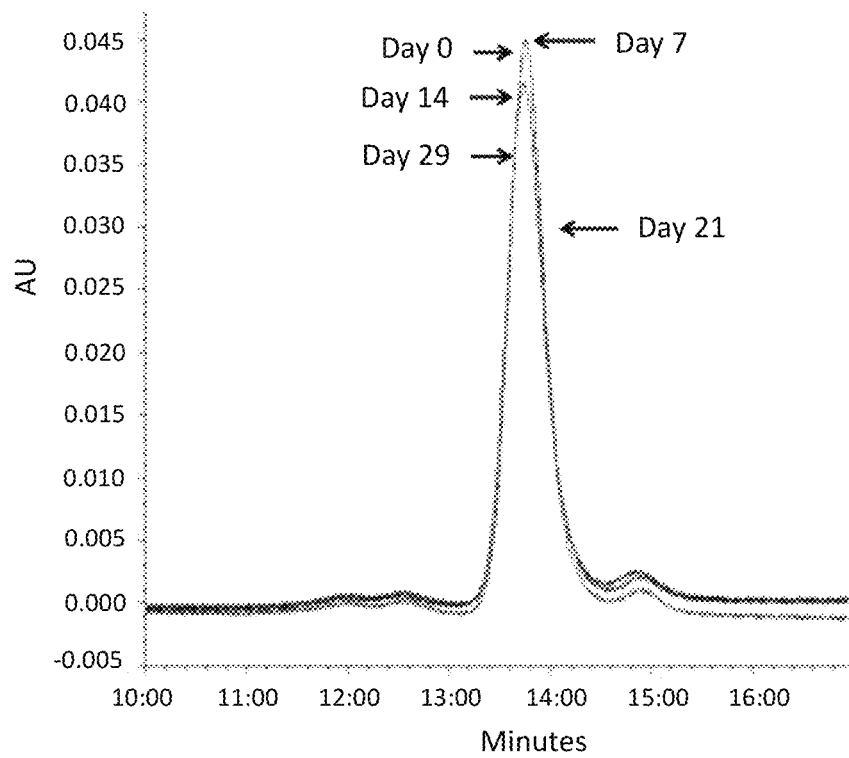
FIG. 11 is an illustration showing the result of detecting and measuring TDC antibody skeleton 4D3-LC-Cys205ins aggregation by SEC-HPLC method, as performed in Example 27.
Figure 12:
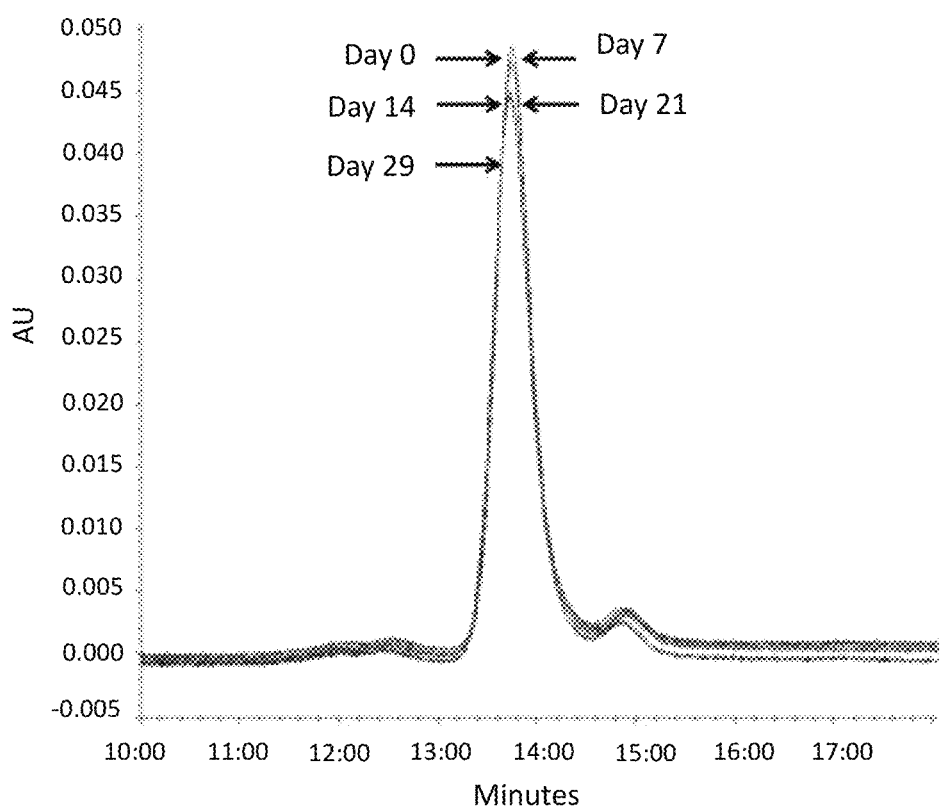
FIG. 12 is an illustration showing the test result of detecting and measuring TDC antibody skeleton 4D3-LC-Cys206ins aggregation by SEC-HPLC method, as performed in Example 27.
Figure 13:
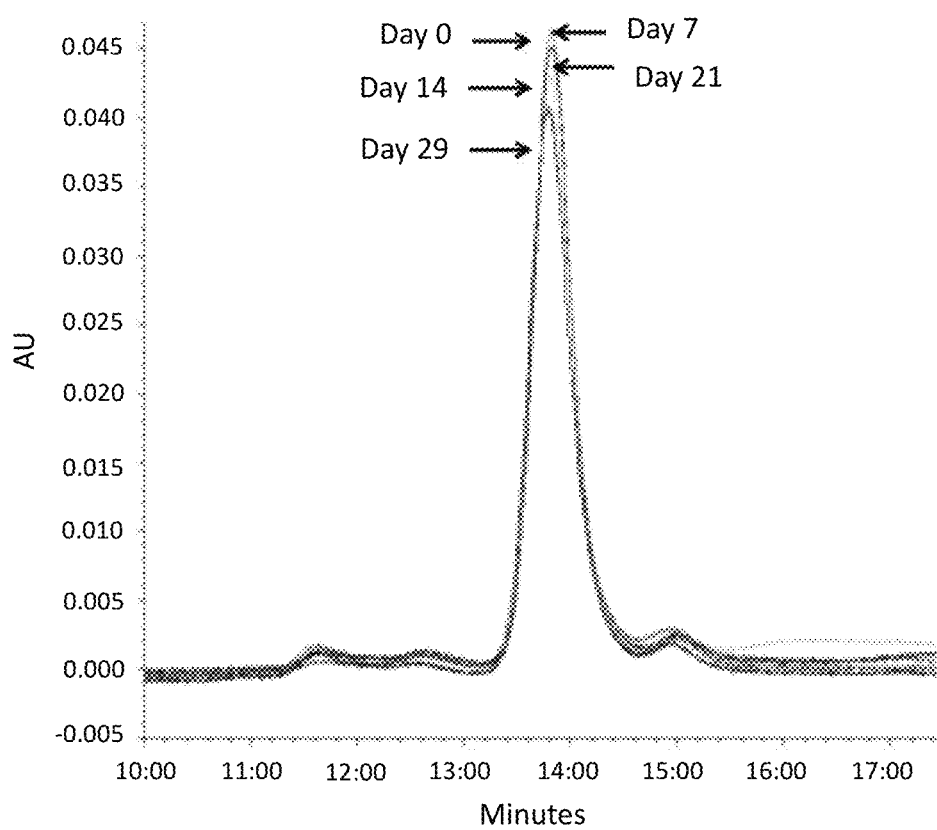
FIG. 13 is an illustration showing the test result of detecting and measuring TDC antibody skeleton 4D3-HC-Cys474ins aggregation by SEC-HPLC method, as performed in Example 27.

Example 26: Measurement of Toxin:Antibody Ratio (DAR, Drug Antibody Ratio) by RP-HPLC The ratio of toxin to antibody was measured by RP-HPLC. The samples treated with DTT were analyzed by reversed-phase hydrophobic high-performance liquid chromatography, and DAR was calculated from the corresponding peak area. One specific method is described in detail as follows:
Column: Proteomix RP-1000 (5 μm, 4.6×100 mm)
Mobile phase: Buffer A: 0.1% TFA aqueous solution; Buffer B: 0.1% acetonitrile solution.
Mobile phase A and mobile phase B were used to elute in a proportional gradient at 80° C., measurement was performed at 214 nm and 280 wavelengths. Based on data gathered in FIG. 9, the site-specific coupled DAR was calculated to be 1.82, showing excellent compound uniformity or homogeneity.

TABLE I

Coupling Efficiency DAR List for ADRs: 2A1-LC-V205C-mc-vc-PAB-MMAE TDC, 2A1-LC-Cys205ins-mc-vc-PAB-MMAE TDC, 2A1-LC-Cys206ins--mc-vc-PAB-MMAE TDC, 2A1-HC-Cys439ins-mc-vc-PAB-MMAE, 4E1-LC-Cys205ins-mc-vc-PAB-MMAE, 4E1-LC-Cys206ins-mc-vc-PAB-MMAE, 4E1-HC-Cys439ins-mc- vc-PAB-MMAE TDC, 4D3-LC-Cys205ins-mc-vc-PAB-MMAE, 4D3-LC-Cys206ins-mc-vc-PAB-MMAE, 4D3-HC-Cys439ins-mc-vc-PAB-MMAE

| | Compounds | DAR |
|---|---|---|
| Site-specific coupling (TDC) | 2A1-LC-V205C-mc-vc-PAB-MMAE TDC | 1.81 |
| | 2A1-LC-Cys205ins-mc-vc-PAB-MMAE TDC | 1.72 |
| | 2A1-LC-Cys206ins-mc-vc-PAB-MMAE TDC | 1.65 |
| | 2A1-HC-Cys439ins-mc-vc-PAB-MMAE TDC | 1.74 |
| | 4E1-LC-Cys205ins-mc-vc-PAB-MMAE TDC | 1.92 |
| | 4E1-LC-Cys206ins-mc-vc-PAB-MMAE TDC | 1.64 |
| | 4E1-HC-Cys439ins-mc-vc-PAB-MMAE TDC | 1.75 |
| | 4D3-LC-Cys205ins-mc-vc-PAB-MMAE TDC | 1.81 |

TABLE I-continued

Coupling Efficiency DAR List for ADRs: 2A1-LC-V205C-mc-vc-PAB-MMAE TDC, 2A1-LC-Cys205ins-mc-vc-PAB-MMAE TDC, 2A1-LC-Cys206ins--mc-vc-PAB-MMAE TDC, 2A1-HC-Cys439ins-mc-vc-PAB-MMAE, 4E1-LC-Cys205ins-mc-vc-PAB-MMAE, 4E1-LC-Cys206ins-mc-vc-PAB-MMAE, 4E1-HC-Cys439ins-mc- vc-PAB-MMAE TDC, 4D3-LC-Cys205ins-mc-vc-PAB-MMAE, 4D3-LC-Cys206ins-mc-vc-PAB-MMAE, 4D3-HC-Cys439ins-mc-vc-PAB-MMAE

| Compounds | DAR |
|---|---|
| 4D3-LC-Cys206ins-mc-vc-PAB-MMAE TDC | 1.74 |
| 4D3-HC-Cys439ins-mc-vc-PAB-MMAE TDC | 1.82 |

TABLE 1 shows that the coupling efficiency of site-directed TDC compounds by cysteine insertion mutation modification is uniformly high (theoretical maximum is 2.0), with DAR≥1.6.

Example 27: Measurement of TDC Antibody Skeleton Aggregation by SEC-HPLC

TDC antibody skeleton samples were stored at 37° C., and their aggregation was analyzed by SEC-HPLC on days 0, 7, 21, and 29, respectively. One specific method is described in detail as follows:
Chromatography columns: TSKgel SuperSW mAb HR (7.8 mm×30 cm),
Mobile phase: 0.1 M sodium sulfate, 0.1 M, pH 6.7 phosphate buffer,
Measurements were performed at 25° C., 280 nm.
As shown in FIGS. 10-13, SEC-HPLC was used to detect and measure the aggregation of TDC antibody skeleton 4D3, 4D3-LC-Cys205ins, 4D3-LC-Cys206ins and 4D3-HC-Cys474ins. The samples were stored at 37° C. for 4 weeks, and the aggregate content remained essentially unchanged.

Using the same detecting and measurement method, the aggregations of the following TDCs are measured: 2A1-LC-V205C-mc-vc-PAB-MMAE TDC, 2A1-LC-Cys205ins-mc-vc-PAB-MMAE TDC, 2A1-LC-Cys206ins-mc-vc-PAB-MMAE TDC, 2A1-HC-Cys474ins-mc-vc-PAB-MMAE, 4E1-LC-Cys205ins-mc-vc-PAB-MMAE, 4E1-LC-Cys206ins-mc-vc-PAB-MMAE 4E1-HC-Cys474ins-mc-vc-PAB-MMAE TDC, 4D3-LC-Cys205ins-mc-vc-PAB-MMAE, 4D3-LC-Cys206ins-mc-vc-PAB-MMAE, 4D3-HC-Cys474ins-mc-vc-PAB-MMAE TDC. The results are shown in TABLE II

TABLE II

TDS target monomer content list for 2A1-LC-V205C-mc-vc-PAB-MMAE TDC, 2A1-LC-Cys205ins-mc-vc-PAB-MMAE TDC, 2A1-LC-Cys206ins--mc-vc-PAB-MMAE TDC and 2A1-HC-Cys439ins-mc-vc-PAB-MMAE, 4E1-LC-Cys205ins-mc-vc-PAB-MMAE, 4E1-LC-Cys206ins-mc-vc-PAB-MMAE, 4E1-HC-Cys439ins-mc-vc-PAB-MMAE TDC, 4D3-LC-Cys205ins-mc-vc-PAB-MMAE, 4D3-LC-Cys206ins-mc-vc-PAB-MMAE, 4D3-HC-Cys439ins-mc-vc-PAB-MMAE

| | Compound | POI % |
|---|---|---|
| Site-specific coupling (TDC) | 2A1-LC-V205C-mc-vc-PAB-MMAE TDC | 96.0% |
| | 2A1-LC-Cys205ins-mc-vc-PAB-MMAE TDC | 90.0% |
| | 2A1-LC-Cys206ins-mc-vc-PAB-MMAE TDC | 90.4% |
| | 2A1-HC-Cys439ins-mc-vc-PAB-MMAE TDC | 90.0% |
| | 4E1-LC-Cys205ins-mc-vc-PAB-MMAE TDC | 98.18% |
| | 4E1-LC-Cys206ins-mc-vc-PAB-MMAE TDC | 94.34% |
| | 4E1-HC-Cys439ins-mc-vc-PAB-MMAE TDC | 95.77% |

TABLE II-continued

TDS target monomer content list for 2A1-LC-V205C-mc-vc-PAB-MMAE TDC, 2A1-LC-Cys205ins-mc-vc-PAB-MMAE TDC, 2A1-LC-Cys206ins--mc-vc-PAB-MMAE TDC and 2A1-HC-Cys439ins-mc-vc-PAB-MMAE, 4E1-LC-Cys205ins-mc-vc-PAB-MMAE, 4E1-LC-Cys206ins-mc-vc-PAB-MMAE, 4E1-HC-Cys439ins-mc-vc-PAB-MMAE TDC, 4D3-LC-Cys205ins-mc-vc-PAB-MMAE, 4D3-LC-Cys206ins-mc-vc-PAB-MMAE, 4D3-HC-Cys439ins-mc-vc-PAB-MMAE

| Compound | POI % |
|---|---|
| 4D3-LC-Cys205ins-mc-vc-PAB-MMAE TDC | 97.27% |
| 4D3-LC-Cys206ins-mc-vc-PAB-MMAE TDC | 96.06% |
| 4D3-HC-Cys439ins-mc-vc-PAB-MMAE TDC | 96.98% |

As shown by TABLE II, the target monomer content of the TDC compound coupled by the inserted cysteine is above 90%.

Example 28: Measurement of Affinities Between Skeletal Antibodies Undergoing Cysteine Site-Directed Mutagenesis and Insertional Mutagenesis and Parental Antibodies and EGFRvIII, Affinities Between 4E1 Antibodies and c-Met, Affinities Between 4D3 Antibodies and Trop2

The relative affinities of 2A1-LC-V205C, 2A1-LC-Cys205ins, 2A1-LC-Cys206ins, 2A1-HC-Cys474ins and 2A1 for EGFRvIII were compared by indirect ELISA. The specific steps are as follows: Recombinant EGFRvIII-His*6 antigen-coated plate was blocked by fish skin gelatin; Antibodies 2A1, 2A1-LC-V205C, 2A1-LC-Cys205ins, 2A1-LC-Cys206ins and 2A1-HC-Cys474ins were respectively diluted by 4 folds gradient with a total of 11 concentrations with the highest concentration being 10 ug/ml; HRP-labeled secondary antibody incubation were performed; after TMB coloration, absorption was detected and measured at 450 nm. The absorption measurement results at A450 were plotted against concentration. The cysteine site-directed mutagenesis or insertion of the mutant antibodies 2A1-LC-V205C, 2A1-LC-Cys205ins, 2A1-LC-Cys206ins and 2A1-HC-Cys474ins retained affinities to EGFRvIII similar to 2A1, as shown by the close $EC_{50}$ values; these results indicate that the site-directed mutagenesis of the light chain V205C on 2A1 antibody, the insertional mutation at position 205 of the light chain of the antibody, the insertional mutation at position 206 of the light chain of the antibody, or the insertion mutation at position 474 of the heavy chain of the antibody does not affect their affinity for the EGFRvIII antigen.

Figure 14:
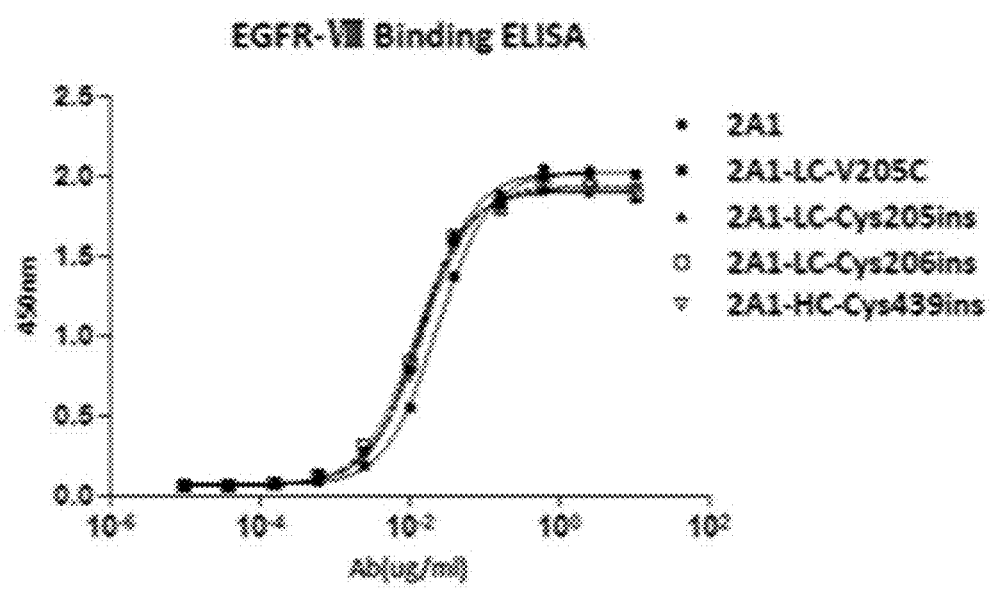
FIG. 14 is an illustration showing the test result of Example 28.

As shown in the FIG. 14, the 2A1-LC-V205C, 2A1-LC-Cys205ins, 2A1-LC-Cys206ins, 2A1-HC-Cys474ins antibodies maintain the affinity of 2A1 to antigen EGFRvIII.

Example 29: Measurement of Affinities of Skeletal Antibodies Undergoing Cysteine Site-Directed Mutagenesis and Insertional Mutagenesis and Linked to Toxin/Drug Towards Connate Antigens, Affinities of 4E1 Antibodies to c-Met, Affinities of 4D3 Antibodies to Trop2

The relative affinities of 4E1-LC-Cys205ins-MVPM, 4E1-LC-Cys206ins-MVPM, 4E1-HC-Cys474ins-MVPM and 4E1 for C-met were compared by indirect ELISA. The specific steps are as follows: Recombinant C-met-His*6 antigen-coated plate was blocked by fish skin gelatin; TDC 4E1-LC-Cys205ins-MVPM, 4E1-LC-Cys206ins-MVPM, 4E1-HC-Cys474ins-MVPM and antibody 4E1 were respectively diluted by 4 folds gradient with a total of 11 concentrations with the highest concentration being 10 ug/ml; HRP-labeled secondary antibody incubation were performed; after TMB coloration, absorption was detected and measured at 450 nm. The absorption measurements at A450 were plotted against concentration, and the result shows that the antibodies harboring cysteine site-directed insertion mutation, TDC 4E1-LC-Cys205ins-MVPM, 4E1-LC-Cys206ins-MVPM, and 4E1-HC-Cys474ins-MVPM, retained their binding affinities to C-met similar to 4E1, as indicated by the close $EC_{50}$ values; which indicates that the insertional mutation at the position 205 or 206 of 4E1 light chain or at the position 474 of 4E1 heavy chain does not affect the binding affinity of the corresponding TDC to the c-met antigen.

The relative affinities of 4D3-LC-Cys205ins-MVPM, 4D3-LC-Cys206ins-MVPM, 4D3-HC-Cys474ins-MVPM and 4D3 for Trop2 were compared by indirect ELISA. The specific steps are as follows:

Recombinant Trop2-His*6 antigen-coated plate was blocked by fish skin gelatin; TDC 4D3-LC-Cys205ins-MVPM, 4D3-LC-Cys206ins-MVPM, 4D3-HC-Cys474ins-MVPM and antibody 4D3 were respectively diluted by 4 folds gradient with a total of 11 concentrations with the highest concentration being 10 ug/ml; HRP-labeled secondary antibody incubation were performed; after TMB coloration, absorption was detected and measured at 450 nm. The absorption measurements at A450 were plotted against concentration. TDC 4D3-LC-Cys205ins-MVPM, 4D3-LC-Cys206ins-MVPM, and 4D3-HC-Cys474ins-MVPM retained their binding affinities to Trop2 similar to that of 4D3, as shown by the close $EC_{50}$ values; which indicates that the insertional mutation at the position 205 or 206 of 4D3 light chain or at the position 474 of 4D3 heavy chain does not affect the binding affinity of the corresponding TDC to the Trop2 antigen.

Figure 15:
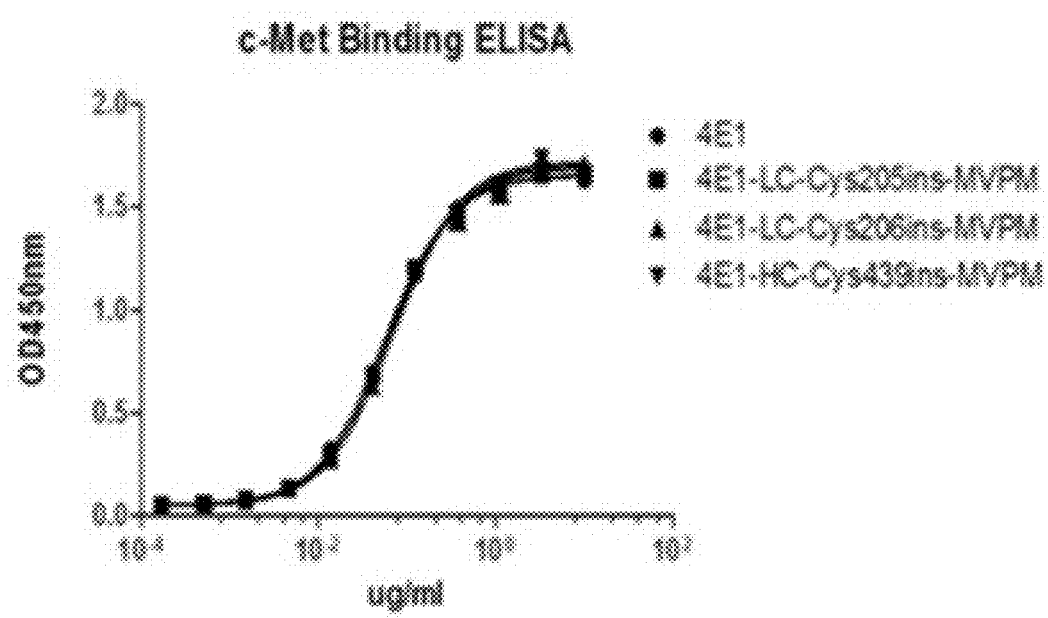
FIG. 15 is an illustration showing the test result of Example 29, showing the affinity measurement between the antigen c-met and the antibody 4E1 and TDC 4E1-LC-Cys205ins-MVPM, 4E1-LC-Cys206ins-MVPM, and 4E1-HC-Cys474ins-MVPM.

As shown in FIG. 15, 4E1-LC-Cys205ins-MVPM, 4E1-LC-Cys206ins-MVPM, 4E1-HC-Cys474ins-MVPM antibodies retained the affinity of 4E1 for antigen c-met.

Figure 16:
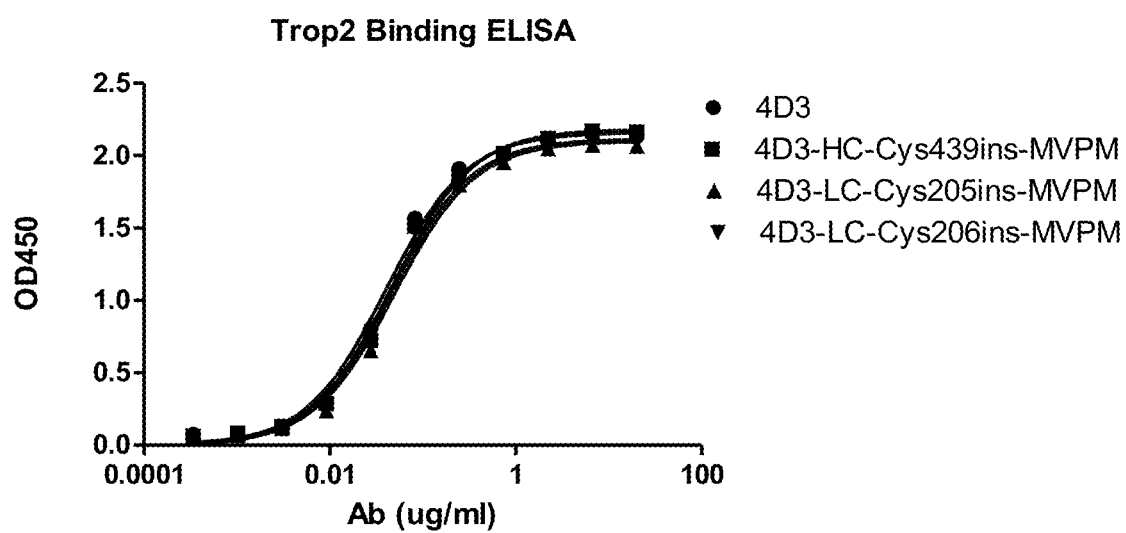
FIG. 16 is an illustration showing the test result of Example 29, showing the affinity measurement between the antigen Trop2 and the antibody 4D3 and TDC 4D3-LC-Cys205ins-MVPM, 4D3-LC-Cys206ins-MVPM, and 4D3-HC-Cys474ins-MVPM.
Figure 17:
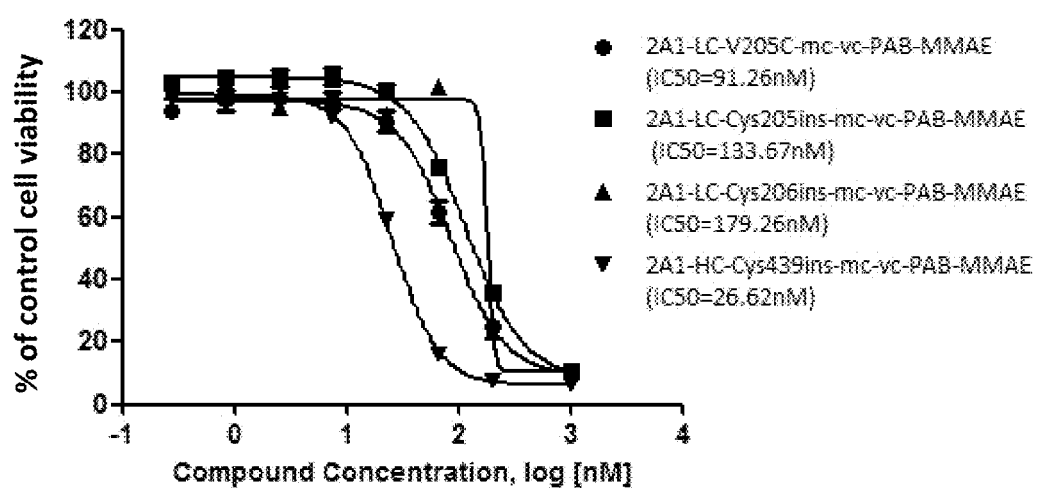
FIG. 17 shows the $IC_{50}$ of cytotoxicity of the ADCs against cancer cells, wherein the ADCs are 2A1-LC-V205C-mc-vc-PAB-MMAE, 2A1-LC-Cys205ins-mc-vc-PAB-MMAE, 2A1-LC-Cys206ins-mc-vc-PAB-MMAE, and 2A1-HC-Cys474ins-mc-vc-PAB-MMA, and the cancer cells are EGFRwt-overexpressing Human squamous cell carcinoma A431.
Figure 18:
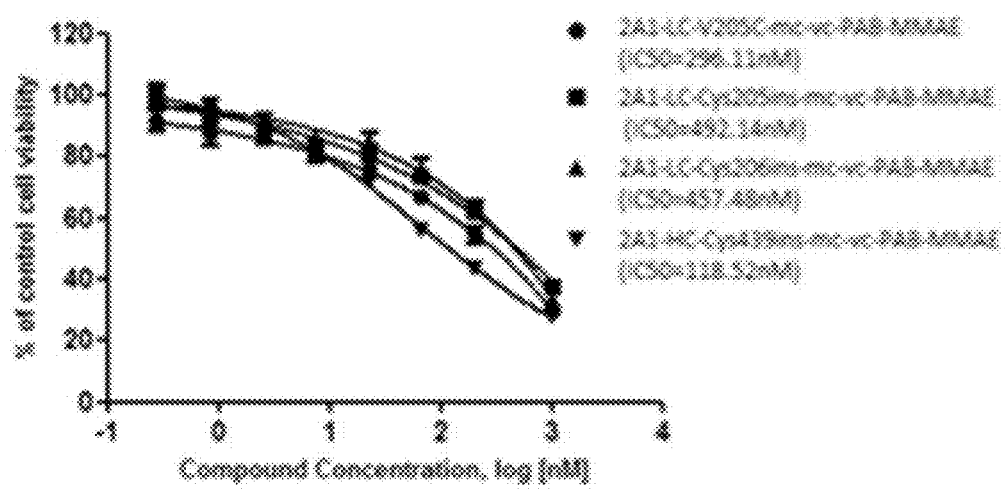
FIG. 18 shows the Iso of cytotoxicity of the ADCs against cancer cells, wherein the ADCs are 2A1-LC-V205C-mc-vc-PAB-MMAE, 2A1-LC-Cys205ins-mc-vc-PAB-MMAE, 2A1-LC-Cys206ins-mc-vc-PAB-MMAE, and 2A1-HC-Cys474ins-mc-vc-PAB-MMAE, and the cancer cells are EGFRvIII-overexpressing Human glioma cell line U87-EGFRvIII.
Figure 19:
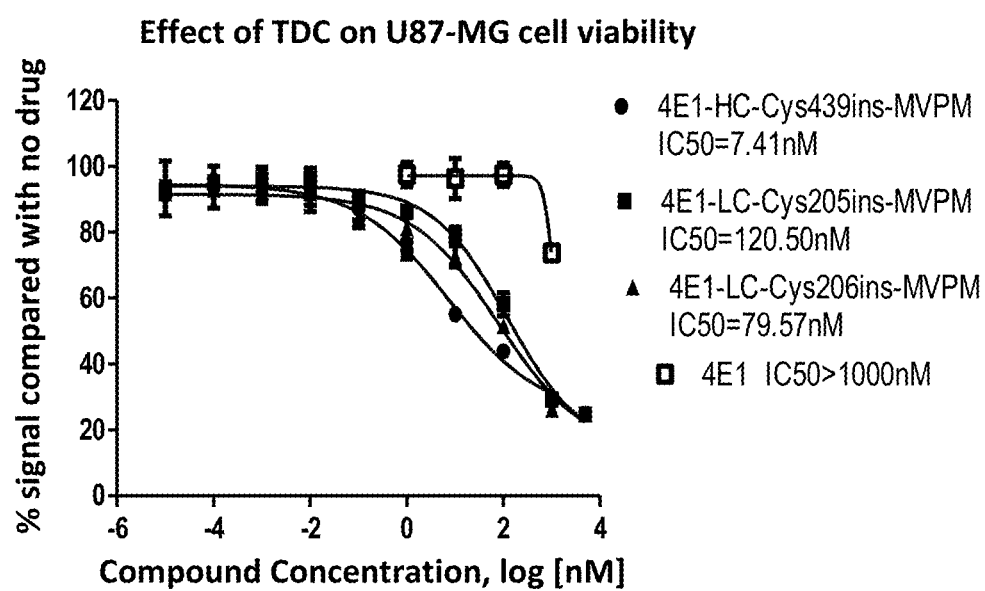
FIG. 19 shows the $IC_{50}$ of cytotoxicity of the ADCs against cancer cells, wherein the ADCs are 4E1-LC-Cys205ins-mc-vc-PAB-MMAE, 4E1-LC-Cys206ins-mc-vc-PAB-MMAE, 4E1-HC-Cys474ins-mc-vc-PAB-MMAE, and 4E1, and the cancer cells are C-met high-expressing malignant glioma cell line U87-MG.
Figure 20:
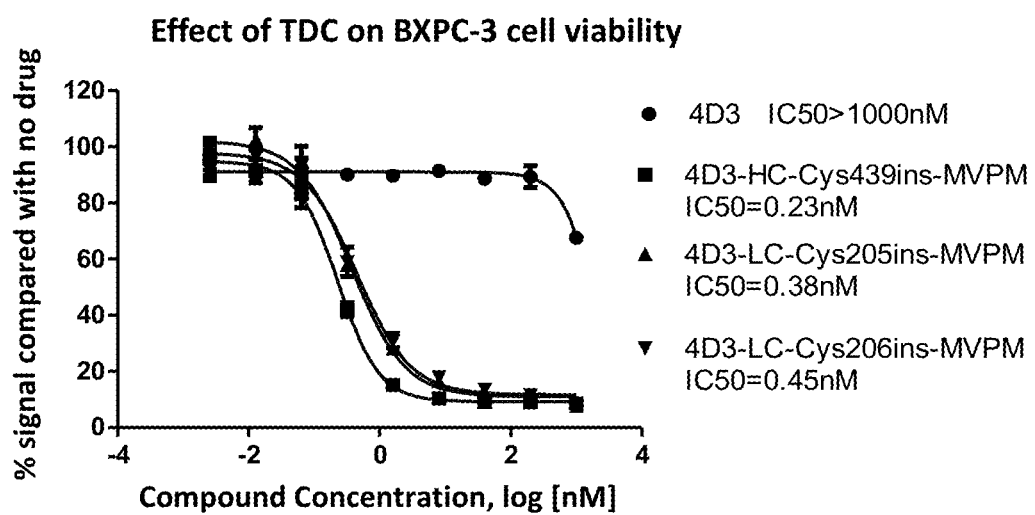
FIG. 20 shows the IC$_{50}$ of cytotoxicity of the ADCs against cancer cells, wherein the ADCs are D3-LC-Cys205ins-mc-vc-PAB-MMAE, 4D3-LC-Cys206ins-mc-vc-PAB-MMAE, 4D3-HC-Cys474ins-mc-vc-PAB-MMAE, and 4D3, and the cancer cells are trop2 high-expressing pancreatic cancer cell line BXPC-3.

As shown in FIG. 16, 4D3-LC-Cys205ins-MVPM, 4D3-LC-Cys206ins-MVPM, 4D3-HC-Cys474ins-MVPM antibodies retained the affinity of 4D3 for the antigen Trop2.

Example 30: Cytotoxicity Pharmaceutical Efficacy Test

TDC cytotoxic activity was determined by the following experimental procedures: TDC was separately added to culture media of human tumor cells in which EGFR was overexpressed or EGFRVIII was expressed, and cell viability was measured after 72 hours of cell culture. Cell-based in vitro assays were used to determine cell viability, cytotoxicity, and TDC-induced apoptosis in the present disclosure.

The in vitro efficacy of the antibody-cytotoxin conjugate was determined by a cell proliferation assay. In one embodiment, the CellTiter 96® Aqueous One Solution Cell Proliferation Assay is commercially available (Promega Corp., Madison, Wis.). The Cell Proliferation Assay (a) is a detection reagent that uses colorimetry to detect the number of viable cells in cell proliferation and cytotoxicity experiments. This reagent contains a novel tetrazolium compound [3-(4,5-dimethylthiazol-2-yl)-5-(3-carboxymethoxyphenyl)-2-(4-sulfophenyl)-2H-tetrazolium, inner salt; MTS] and an electronic coupling agent (phenazine ethosulfate; PES). PES has enhanced chemical stability, which allows it to be mixed with MTS to form a stable solution. This convenient "single solution" mode is based on the first generation CellTiter 96® AQueous Assay, in which the electronic coupling agent PMS and MTS solution are supplied separately. MTS (Owen's reagent) is biologically reduced by cells to a colored formazan product that is directly soluble in the medium (FIG. 1). This transformation is most likely accomplished by the action of NADPH or NADH produced by dehydrogenase in metabolically active cells. For detection, simply add a small amount of CellTiter 96® AQueous One Solution Reagent directly to the culture medium well, incubate for 1-4 hours, and then read the absorbance at 490 nm with a microplate reader.

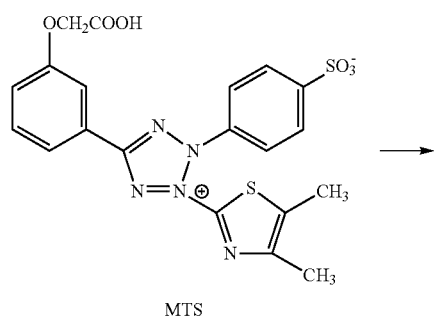

MTS

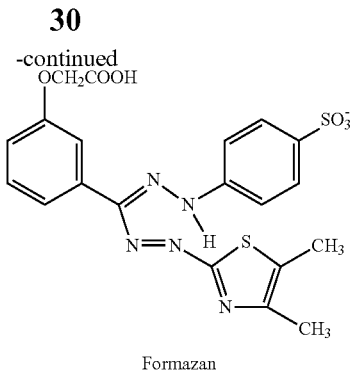

Formazan

The amount of formazan product detected at 490 nm is directly proportional to the number of viable cells in the culture. Since the MTS hyperthyroid product is soluble in tissue culture media, the CellTiter 96® AQueous One Solution Assay has fewer steps than the MTT or INT method.

In the present disclosure, A431 (EGFR overexpressing cells), U87-EGFRVIII (EGFR mutant stable cell line), U87-MG (glioblastoma cell line with highly expressed c-Met) and BXPC-3 (pancreatic cancer cell line with high expression of Trop2) are used as research systems for in vitro drug efficacy testing. In a 96-well plate, cell plating was performed at a concentration of 6000/well, and after 24 hours, antibody administration was performed. The initial concentrations of various TDCs corresponding to A431, U87-EGFRVIII cell lines were 10 μM, which were sequentially diluted according to a 5-fold gradient. The initial concentrations of various TDCs corresponding to U87-MG and BXPC-3 cell lines were 1 μM, which were sequentially diluted according to a 5-fold gradient. MTS assay for cell viability were performed after 72 hours of treatment

TABLE III

Cytotoxicity $IC_{50}$ detection results of TDC, ADC on EGFRwt overexpressing cell line A431 and EGFRvIII expression stable strain U87-EGFRVIII

| | | MTS | | | |
| --- | --- | --- | --- | --- | --- |
| | Compounds | A431 | U87MG-EGFRvIII | U87-MG | BXPC-3 |
| Antibody 2A1 | 2A1 | >10 μM | >10 μM | / | / |
| | 2A1-LC-V205C | >10 μM | >10 μM | / | / |
| | 2A1-LC-Cys205ins | >10 μM | >10 μM | / | / |
| | 2A1-LC-Cys206ins | >10 μM | >10 μM | / | / |
| | 2A1-HC-Cys439ins | >10 μM | >10 μM | / | / |
| Site-directed coupling (TDC) | 2A1-LC-V205C-mc-vc-PAB-MMAE | 92.16 nM | 296.11 nM | / | / |
| | 2A1-LC-Cys205ins-mc-vc-PAB-MMAE | 133.67 nM | 492.14 nM | / | / |
| | 2A1-LC-Cys206ins-mc-vc-PAB-MMAE | 179.26 nM | 457.48 nM | / | / |
| | 2A1-HC-Cys439ins-mc-vc-PAB-MMAE | 26.62 nM | 118.52 nM | / | / |
| Antibody 4E1 | 4E1 | / | / | >1 μM | / |
| Site-directed coupling (TDC) | 4E1-LC-Cys205ins-mc-vc-PAB-MMAE | / | / | 120.50 nM | / |
| | 4E1-LC-Cys206ins-mc-vc-PAB-MMAE | / | / | 79.57 nM | / |
| | 4E1-HC-Cys439ins-mc-vc-PAB-MMAE | / | / | 7.41 nM | / |

TABLE III-continued

Cytotoxicity IC$_{50}$ detection results of TDC, ADC on EGFRwt overexpressing cell line A431 and EGFRvIII expression stable strain U87-EGFRVIII

| | | MTS | | | |
|---|---|---|---|---|---|
| | Compounds | A431 | U87MG-EGFRvIII | U87-MG | BXPC-3 |
| Antibody 4D3 | 4D3 | / | / | / | >1 μM |
| Site-directed coupling (TDC) | 4D3-LC-Cys205ins-mc-vc-PAB-MMAE | / | / | / | 0.38 nM |
| | 4D3-LC-Cys206ins-mc-vc-PAB-MMAE | / | / | / | 0.45 nM |
| | 4D3-HC-Cys439ins-mc-vc-PAB-MMAE | / | / | / | 0.23 nM |

The data from the TABLE III shows that, 2A1-LC-V205C-mc-vc-PAB-MMAE TDC, 2A1-LC-Cys205Cins-mc-vc-PAB-MMAE TDC, 2A1-LC-Cys206ins-mc-vc-PAB-MMAE TDC, and 2A1-HC-Cys474ins-mc-vc-PAB-MMAE TDC have comparable cytotoxic activity to EGFRwt overexpressing cell line A431 and EGFRvIII expression stable strain U87-EGFRVIII, and 474 inserted mutant TDC's activity is slightly higher than 205 and 206 insertion mutant TDC.

There was a certain correlation between cytotoxic activity and coupling position for the 4E1-LC-Cys205ins-mc-vc-PAB-MMAE TDC, 4E1-LC-Cys206ins-mc-vc-PAB-MMAE TDC and 4E1-HC-Cys474ins-mc-vc-PAB-MMAE TDC in U87-MG cells. The TDC activity of the 474 inserted mutant was slightly better than those of the 205 and 206 insertion mutants. The activity of TDC was significantly better than that of the parental antibody.

The cytotoxic activity of 4D3-LC-Cys205ins-mc-vc-PAB-MMAE TDC, 4D3-LC-Cys206ins-mc-vc-PAB-MMAE TDC and 4D3-HC-Cys474ins-mc-vc-PAB-MMAE TDC in pancreatic cancer cell line BXPC-3 was comparable or similar to each other, and the TDC activity of the 474 inserted mutant was slightly better than those of the 205 and 206 insertion mutant TDCs, and the activity of TDC was significantly better than that of the parental antibody.

Example 31: Plasma Stability Test

Figure 21:
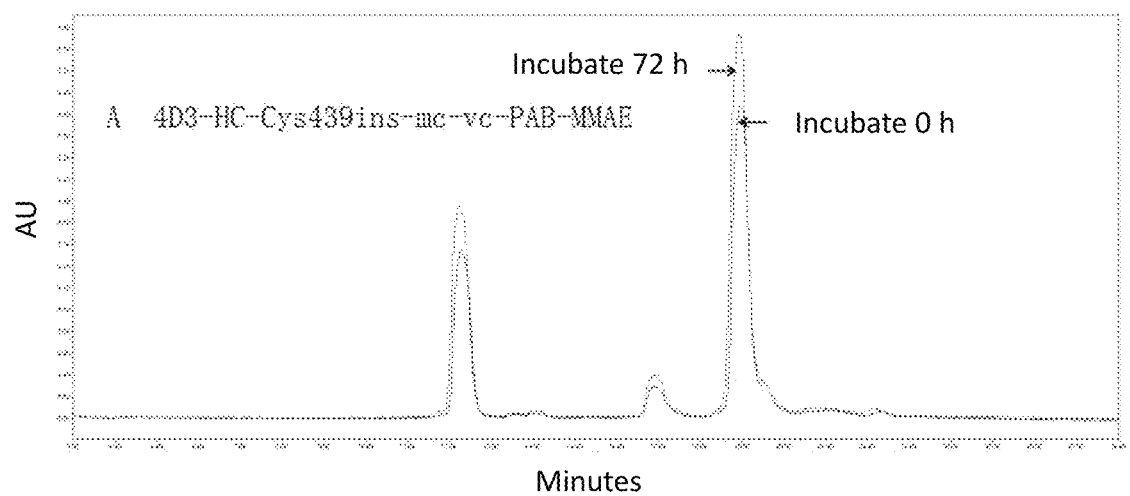
FIG. 21 is an illustration showing the test result of stability measurement in human plasma for 4D3-LC-Cys205ins-mc-vc-PAB-MMAE.
Figure 22:
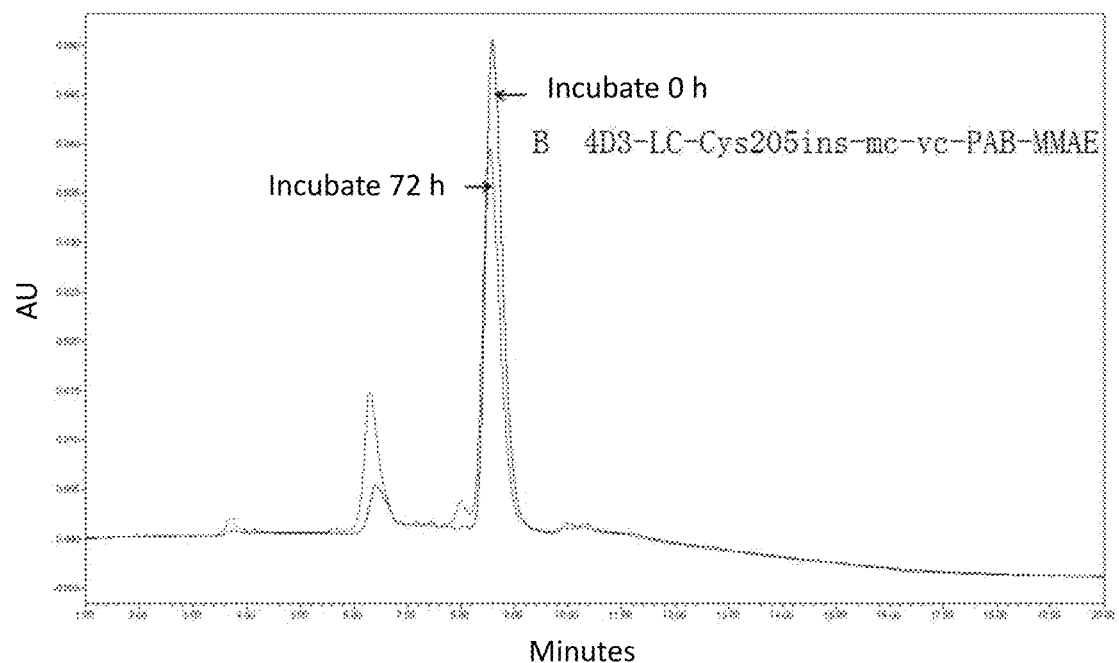
FIG. 22 is an illustration showing the test result of stability measurement in human plasma for 4D3-LC-Cys206ins-mc-vc-PAB-MMAE.
Figure 23:
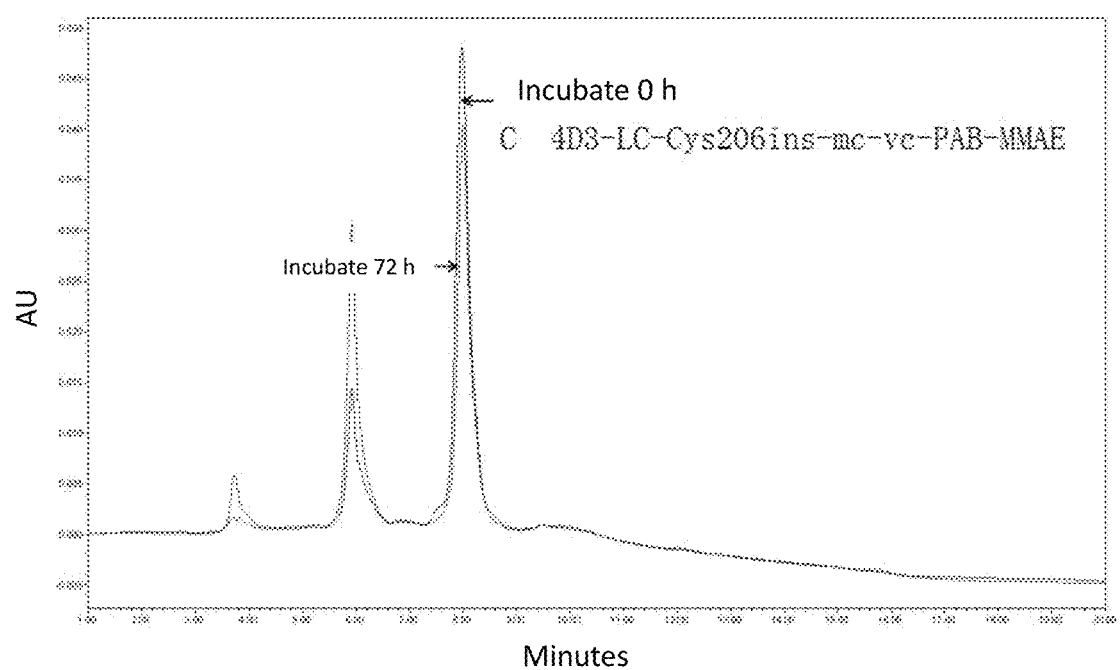
FIG. 23 is an illustration showing the test result of stability measurement in human plasma for 4D3-HC-Cys474ins-mc-vc-PAB-MMAE.

Take a certain amount of ADC sample, add it to human plasma from which human IgG has been removed, repeat 2 tubes for each ADC, incubate in a 37° C. water bath, incubate for 0 h, 72 h, take ADC samples, add 100 μl ProteinA (MabSelect SuRe™ LX Lot: #10221479 GE washed with PBS), shaken for 2 h with a vertical mixer, and subjected to a washing and elution step to obtain an ADC after incubation. The samples, which had undergone incubation for a certain time, were subjected to HIC-HPLC and RP-HPLC to determine the plasma stability of the samples. FIGS. 21-23 shows the result of the test for in human plasma stability for the 4D3-LC-Cys205ins-mc-vc-PAB-MMAE TDC, 4D3-LC-Cys206ins-mc-vc-PAB-MMAE TDC and 4D3-HC-Cys474ins-mc-vc-PAB-MMAE TDC. The detection method for 4D3-HC-Cys474ins-mc-vc-PAB-MMAE was RP-HPLC; The detection method for 4D3-LC-Cys205ins-mc-vc-PAB-MMAE TDC and 4D3-LC-Cys206ins-mc-vc is HIC-HPLC.

Figure 24:
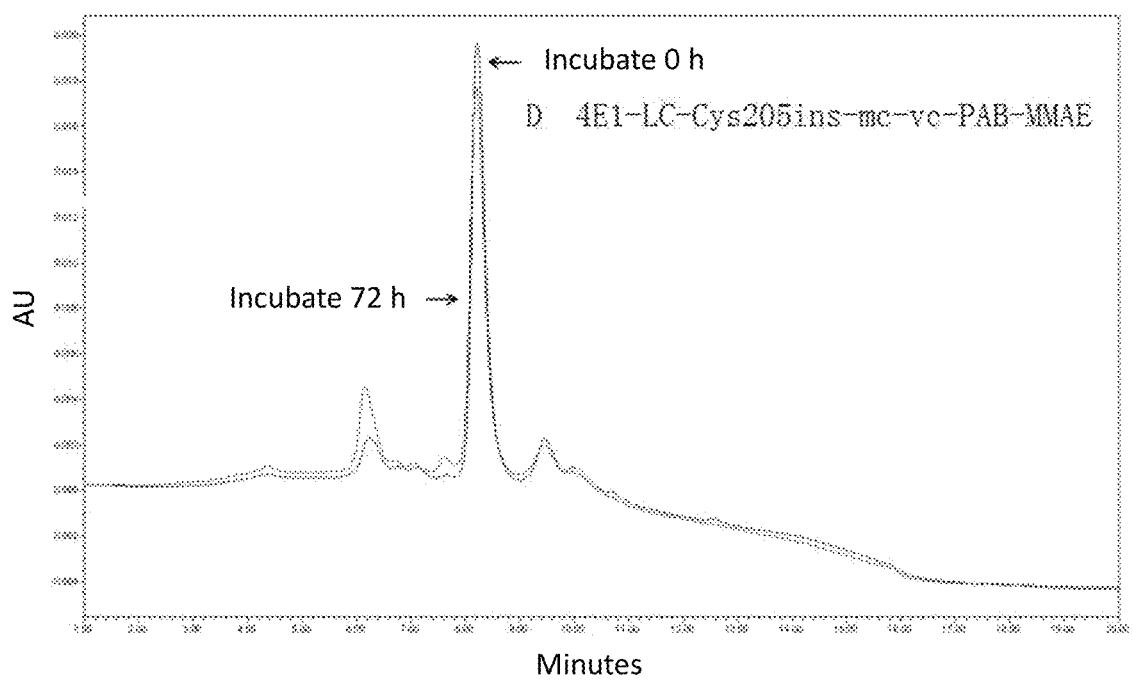
FIG. 24 is an illustration showing the test result of stability measurement in human plasma for 4E1-LC-Cys205ins-mc-vc-PAB-MMAE.
Figure 25:
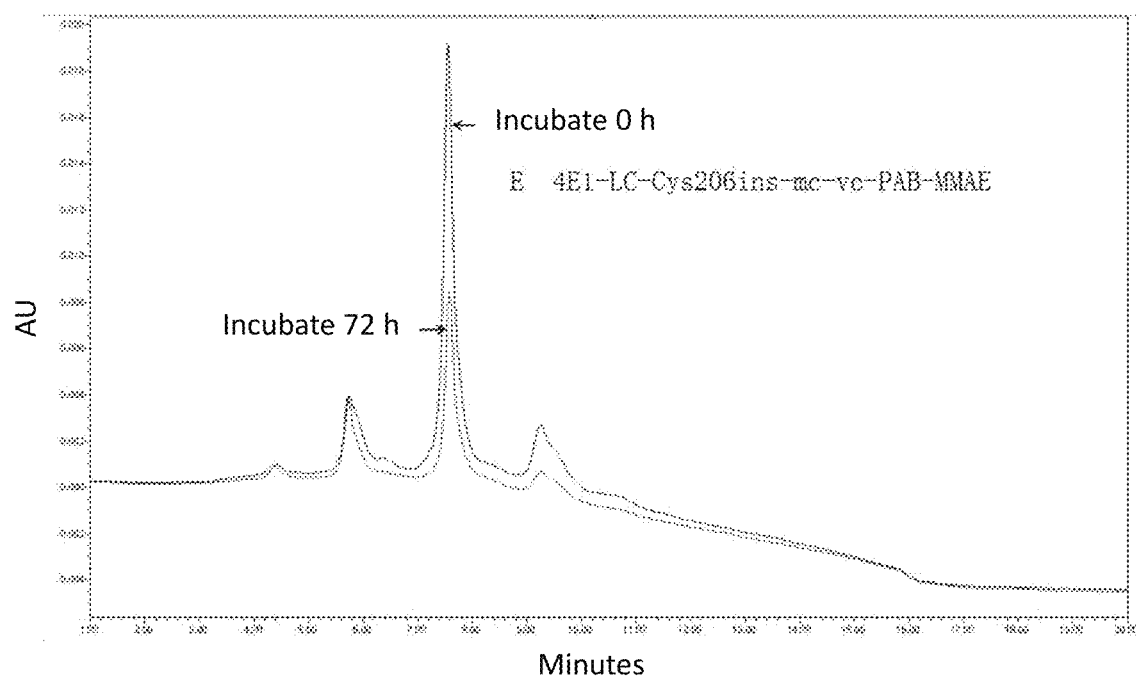
FIG. 25 is an illustration showing the test result of stability measurement in human plasma for 4E1-LC-Cys206ins-mc-vc-PAB-MMAE.
Figure 26:
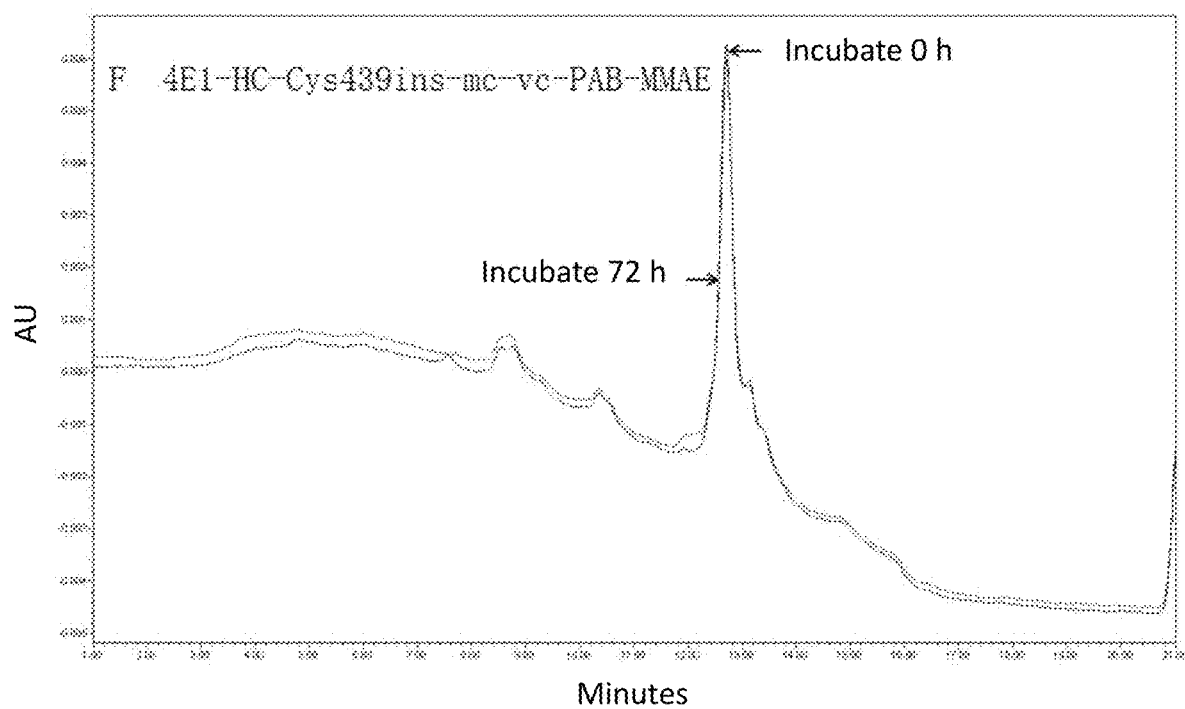
FIG. 26 is an illustration showing the test result of stability measurement in human plasma for 4E1-HC-Cys474ins-mc-vc-PAB-MMAE.

FIGS. 24-26 shows the result of the test for in human plasma stability for the 4E1-LC-Cys205ins-mc-vc-PAB-MMAE TDC, 4E1-LC-Cys206ins-mc-vc-PAB-MMAE TDC and 4E1-HC-Cys474ins-mc-vc-PAB-MMAE TDC. The detection method is HIC-HPLC

TABLE IV

TDC plasma stability test result (calculated by the change of DAR)

| | | DAR | |
|---|---|---|---|
| | Compound | 37° C. 0 h | 37° C. 72 h |
| Site-directed coupling (TDC) | 4E1-LC-Cys205ins-mc-vc-PAB-MMAE TDC | 1.89 | 1.77 |
| | 4E1-LC-Cys206ins-mc-vc-PAB-MMAE TDC | 1.81 | 1.62 |
| | 4E1-HC-Cys439ins-mc-vc-PAB-MMAE TDC | 1.85 | 1.83 |
| | 4D1-LC-Cys205ins-mc-vc-PAB-MMAE TDC | 1.86 | 1.71 |
| | 4D3-LC-Cys206ins-mc-vc-PAB-MMAE TDC | 1.76 | 1.52 |
| | 4D3-HC-Cys439ins-mc-vc-PAB-MMAE TDC | 1.81 | 1.80 |

The above TDCs were stable after being incubated at 37° C. for 72 hours in human plasma samples and had good drug-forming properties. In comparison, TDC with 474 insertion mutations had the best stability, followed by TDC with 205 and 206 insertion mutations.

Example 32: Tumor-Bearing Mice Pharmaceutical Efficacy Test

In the present disclosure, a BXPC-3 tumor-bearing mouse model was established to evaluate the in vivo efficacy of TDC and parental antibodies. In one embodiment, 3×10$^6$ BXPC-3 cells were subcutaneously injected into the back side of 4-8 weeks old BALB/c nude mice, and the average tumor size of the mice was grown to 400-500 mm$^3$, the mice were randomly grouped, 5 mice in each group. On Day 0 and Day 7, 4D3-LC-Cys205ins-mc-vc-PAB-MMAE TDC, 4D3-LC-Cys206ins-mc-vc-PAB-MMAE TDC and 4D3-HC-Cys474ins-mc-vc-PAB-MMAE TDC were administered in a single intravenous dose at a dose of 5 mg/kg, and the parental antibody 4D3 was administered at a dose of 5 mg/kg. Data A shows the mean tumor volume±SE at the time of measurement, and data B shows the average body weight of the mouse at the time of measurement±SE.

Figure 27:
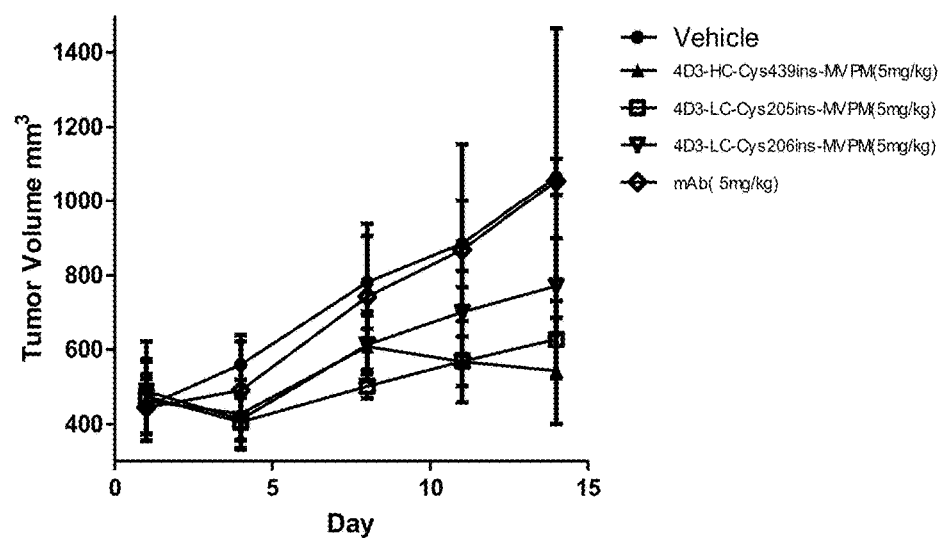
FIG. 27A is an illustration showing the test result of pharmacodynamic effect measurement for 4D3-LC-Cys205ins-mc-vc-PAB-MMAE, 4D3-LC-Cys206ins-mc-vc-PAB-MMAE, 4D3-HC-Cys474ins-mc-vc-PAB-MMAE, and 4D3 parental antibody in tumor-bearing mice.

FIG. 27 shows the results of the test on the efficacy in the tumor-bearing mice for 4D3-LC-Cys205ins-mc-vc-PAB-MMAE TDC, 4D3-LC-Cys206ins-mc-vc-PAB-MMAE TDC, 4D3-HC-Cys474ins-mc-vc-PAB-MMAE TDC, and 4D3. TDC showed significant anti-tumor effect in vivo compared to the parental antibodies.

Figure 28:
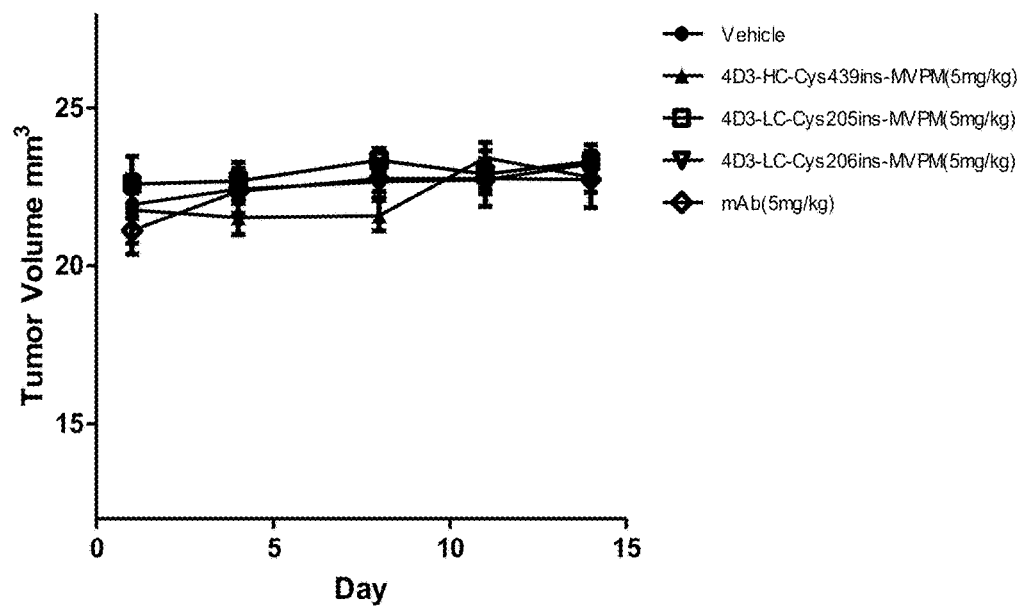
FIG. 28B is an illustration showing the test result of pharmacodynamic effect measurement for 4D3-LC-Cys205ins-mc-vc-PAB-MMAE, 4D3-LC-Cys206ins-mc-vc-PAB-MMAE, 4D3-HC-Cys474ins-mc-vc-PAB-MMAE, 4D3-HC-Cys474ins-mc-vc-PAB-MMAE, and 4D3 parental antibody in tumor-bearing mice.

FIG. 28 shows the results of the test on the efficacy in the tumor-bearing mice for 4D3-LC-Cys205ins-mc-vc-PAB- MMAE TDC, 4D3-LC-Cys206ins-mc-vc-PAB-MMAE TDC, 4D3-HC-Cys474ins-mc-vc-PAB-MMAE TDC and 4D3 parental antibody. There was no significant change in the body weight of the mice, which proved that the TDCs have no or minor toxicity in vivo.

The disclosure is not limited to the scope of the specific embodiments disclosed in the embodiments, which are intended to illustrate several aspects of the disclosure, and any embodiments that are functionally equivalent are within the scope of the disclosure. In fact, various modifications of the disclosure are obvious to those skilled in the art and are in the scope of the appended claims.

TABLE V

| amino acids | |
| --- | --- |
| English Name | Symbol or Abbreviation |
| Alanine | A or Ala |
| Arginine | R or Arg |
| Asparagine | N or Asn |
| Aspartic acid | D or Asp |
| Cysteine | C or Cys |
| Glutamine | Q or Gln |
| Glutamic acid | E or Glu |
| Glycine | G or Gly |
| Histidine | H or His |
| Isoleucine | I or Ile |
| Leucine | L or Leu |
| Lysine | K or Lys |
| Methionine | M or Met |
| Phenylalanine | F or Phe |
| Proline | P or Pro |
| Serine | S or Ser |
| Threonine | T or Thr |
| Tryptophan | W or Trp |
| Tyrosine | Y or Tyr |
| Valine | V or Val | heavy chain constant region (Fc) DNA sequence
>IgG1-Fc
SEQ ID NO: 1
GCTAGCACCAAGGGCCCATCGGTCTTCCCCCTGGCACCCTCCTCCAAGAGC

ACCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTG

GTGACCGTGCCCTCCAGCAGCTTGGGCACCCAGACCTACATCTGCAACGTG

AATCACAAGCCCAGCAACACCAAGGTGGACAAGAGAGTTGAGCCCAAATCT

TGTGACAAAACTCACACATGCCCACCGTGCCCAGCACCTGAACTCCTGGGG

GGACCGTCAGTCTTCCTCTTCCCCCCAAAACCCAAGGACACCCTCATGATC

TCCCGGACCCCTGAGGTCACATGCGTGGTGGTGGACGTGAGCCACGAAGAC

CCTGAGGTCAAGTTCAACTGGTACGTGGACGGCGTGGAGGTGCATAATGCC

AAGACAAAGCCGCGGGAGGAGCAGTACAACAGCACGTACCGTGTGGTCAGC

GTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAA

GCCAAAGGGCAGCCCCGAGAACCACAGGTGTACACCCTGCCCCCATCCCGG

GATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCTC

TATAGCAAGCTCACCGTGGACAAGAGCAGGTGGCAGCAGGGGAACGTCTTC

TCATGCTCCGTGATGCATGAGGCTCTGCACAACCACTACACGCAGAAGAGC

CTCTCCCTGTCTCCGGGTAAA heavy chain constant region (Fc) amino acid sequence
>IgG1-Fc
SEQ ID NO: 2
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKRVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK light chain constant region (Kappa) DNA sequence
>LC-Kappa
SEQ ID NO: 3
ACGGTGGCTGCACCATCTGTCTTCATCTTCCCGCCATCTGATGAGCAGTTG

AAATCTGGAACTGCCTCTGTTGTGTGCCTGCTGAATAACTTCTATCCCAGA

GAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGC

AGCACCCTGACGCTGAGCAAAGCAGACTACGAGAAACACAAAGTCTACGCC

TGCGAAGTCACCCATCAGGGCCTGAGCTCGCCCGTCACAAAGAGCTTCAAC

AGGGGAGAGTGTTAG light chain constant region (Kappa) amino acid sequence
>LC-Kappa
SEQ ID NO: 4
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFN

RGEC

2A1-LC-Cys205ins light chain constant region (Kappa) DNA sequence
>LC-Cys205ins-Kappa
SEQ ID NO: 5
ACGGTGGCTGCACCATCTGTCTTCATCTTCCCGCCATCTGATGAGCAGTTG

AAATCTGGAACTGCCTCTGTTGTGTGCCTGCTGAATAACTTCTATCCCAGA

GAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGC

AGCACCCTGACGCTGAGCAAAGCAGACTACGAGAAACACAAAGTCTACGCC

TGCGAAGTCACCCATCAGGGCCTGAGCTCGCCCTGCGTCACAAAGAGCTTC

AACAGGGGAGAGTGTTAG

LC-Cys205ins light chain constant region (Kappa) amino acid sequence
>LC-Cys205ins-Kappa
SEQ ID NO: 6
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPCVTKSF

NRGEC wherein, the C in the GLSSPCVTKSF (SEQ ID NO:13) is the site-specific conjugation position. In one embodiment, the cysteine is conjugated with mc-vc-PAB-payload site-specifically.

```
LC-Cys206ins light chain constant region
(Kappa) DNA sequence
>LC-Cys206ins-Kappa
                                        SEQ ID NO: 7
ACGGTGGCTGCACCATCTGTCTTCATCTTCCCGCCATCTGATGAGCAGTTG

GAGGCCAAAGTACAGTGGAAGGTGGATAACGCCCTCCAATCAAATCTGGAA

CTGCCTCTGTTGTGTGCCTGCTGAATAACTTCTATCCCAGAGGGTAACTCC

CAGGAGAGTGTCACAGAGCAGGACAGCAAGGACAGCACCTACAGCCTCAGC

AGCACCCTGACGCTGAGCAAAGCAGACTACGAGAAACACAAAGTCTACGCC

TGCGAAGTCACCCATCAGGGCCTGAGCTCGCCCGTCTGCACAAAGAGCTTC

AACAGGGGAGAGTGTTAG

LC-Cys206ins light chain constant region (Kappa)
amino acid sequence
>LC-Cys206ins-Kappa
                                        SEQ ID NO: 8
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVCTKSF

NRGEC
``` wherein, the C in the GLSSPVCTKSF (SEQ ID NO:14) is the site-specific conjugation position. In one embodiment, the cysteine is conjugated with mc-vc-PAB-payload site-specifically.

```
IgG1-Fc-Cys439ins heavy chain constant region (Fc)
DNA sequence
>IgG1-Fc-Cys439ins
                                        SEQ ID NO: 9
GCTAGCACCAAGGGCCCATCGGTCTTCCCCCTGGCACCCTCCTCCAAGAGC

ACCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTG

GTGACCGTGCCCTCCAGCAGCTTGGGCACCCAGACCTACATCTGCAACGTG

AATCACAAGCCCAGCAACACCAAGGTGGACAAGAGAGTTGAGCCCAAATCT

TGTGACAAAACTCACACATGCCCACCGTGCCCAGCACCTGAACTCCTGGGG

GGACCGTCAGTCTTCCTCTTCCCCCCAAAACCCAAGGACACCCTCATGATC

TCCCGGACCCCTGAGGTCACATGCGTGGTGGTGGACGTGAGCCACGAAGAC

CCTGAGGTCAAGTTCAACTGGTACGTGGACGGCGTGGAGGTGCATAATGCC

AAGACAAAGCCGCGGGAGGAGCAGTACAACAGCACGTACCGTGTGGTCAGC

GTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAA

GCCAAAGGGCAGCCCCGAGAACCACAGGTGTACACCCTGCCCCCATCCCGG

GATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCTC

TATAGCAAGCTCACCGTGGACAAGAGCAGGTGGCAGCAGGGGAACGTCTTC

TCATGCTCCGTGATGCATGAGGCTCTGCACAACCACTACACGCAGAAGAGC

CTCTCCTGCCTGTCTCCGGGTAAA

IgG1-Fc-Cys439ins heavy chain constant region (Fc)
amino acid sequence
>IgG1-Fc-Cys439ins
                                        SEQ ID NO: 10
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKRVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSCLSPGK
```

Wherein the C in the TQKSLSCLSPGK (SEQ ID NO:15) sequence is the site-specific conjugation/coupling position, and undergoes site-specific conjugation with mc-vc-PAB-payload.

```
LC-V205C light chain constant region (Kappa) DNA
sequence
>LC-V205C-Kappa
                                        SEQ ID NO: 11
ACGGTGGCTGCACCATCTGTCTTCATCTTCCCGCCATCTGATGAGCAGTTG

AAATCTGGAACTGCCTCTGTTGTGTGCCTGCTGAATAACTTCTATCCCAGA

GAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGC

AGCACCCTGACGCTGAGCAAAGCAGACTACGAGAAACACAAAGTCTACGCC

TGCGAAGTCACCCATCAGGGCCTGAGCTCGCCCTGCACAAAGAGCTTCAAC

AGGGGAGAGTGTTAG

LC-V205C light chain constant region (Kappa) amino
acid sequence
>LC-V205C-Kappa
                                        SEQ ID NO: 12
TVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPCTKSFN

RGEC
```

Wherein the C in the GLSSPCTKSF (SEQ ID NO:16) sequence is the site-specific conjugation/coupling position, and undergoes site-specific conjugation with mc-vc-PAB-payload.

```
LC-V205C light chain constant region (Kappa) amino
acid sequence
                                        SEQ ID NO: 13
GLSSPCVTKSF LC-V206C light chain constant region (Kappa) amino
acid sequence
                                        SEQ ID NO: 14
GLSSPVCTKS Heavy chain amino acid sequence
                                        SEQ ID NO: 15
TQKSLSCLSPGK
```

What is claimed is:

1. A cysteine modified antibody-cytotoxin conjugate, comprising an antibody and a cytotoxin, wherein the antibody comprises an inserted cysteine at a cysteine insertion site such that the antibody comprises a light chain comprising the amino acid sequence GLSSPCVTKSF (SEQ ID NO: 13), a light chain comprising the amino acid sequence GLSSPVCTKSF (SEQ ID NO: 14), or a heavy chain comprising the amino acid sequence TQKSLSCLSPGK (SEQ ID NO: 15), and wherein C is the inserted cysteine, wherein the inserted cysteine comprises a thiol group, wherein the cytotoxin is conjugated to the thiol group through a linker.

2. The cysteine modified antibody-cytotoxin conjugate of claim 1, wherein the antibody comprises a light chain, wherein the light chain comprises the amino acid sequence of SEQ ID NO: 13.

3. The cysteine modified antibody-cytotoxin conjugate of claim 1, wherein the antibody comprises a light chain, wherein the light chain comprises the amino acid sequence of SEQ ID NO: 14.

4. The cysteine modified antibody-cytotoxin conjugate of claim 1, wherein the antibody comprises a heavy chain, wherein the heavy chain comprises the amino acid sequence of SEQ ID NO: 15.

5. The cysteine modified antibody-cytotoxin conjugate of claim 1, wherein the cytotoxin is selected from Monomethyl auristatin E (MMAE), Monomethyl Auristatin F (MMAF), Pyrrolobenzodiazepines (PBD), antineoplastic drug SN-38, Doxycycline (Dox), or a derivative thereof, wherein the formulae of MMAE, MMAF, PBD, SN-38 and Dox are respectively:

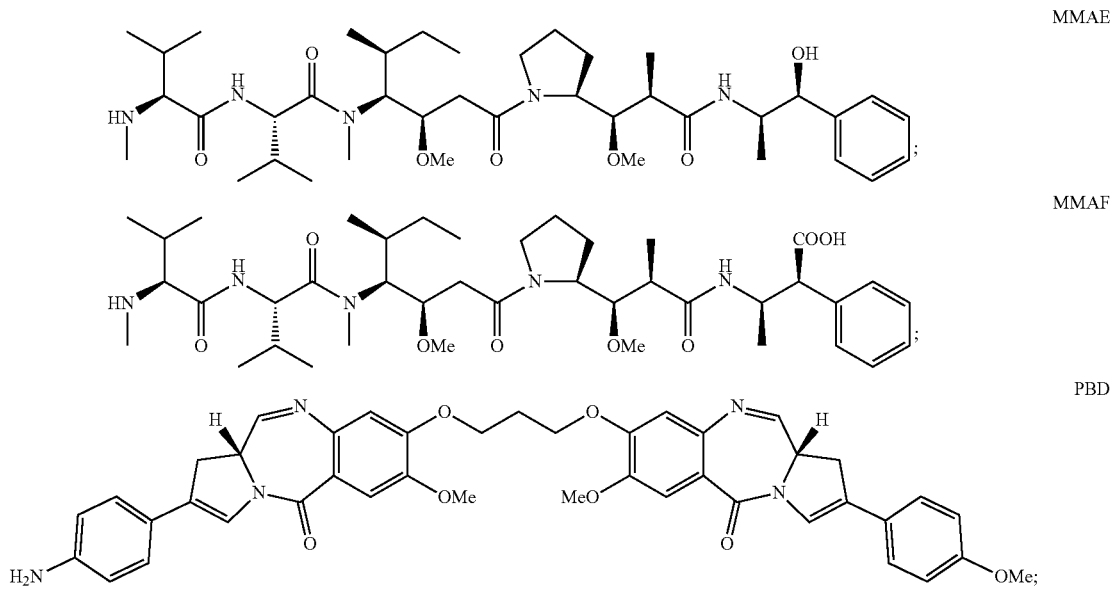

-continued

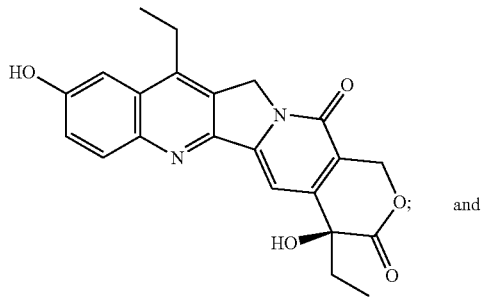
SN-38

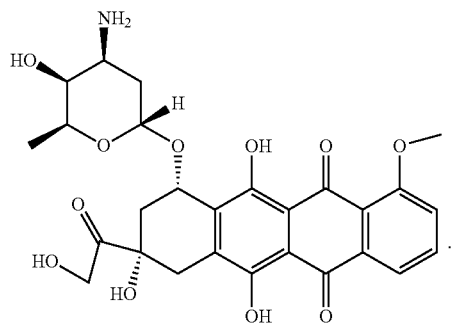
DOX and

6. A method for preparing the cysteine modified antibody-cytotoxin conjugate of claim 1, comprising,
reducing the antibody with a reducing agent to provide a reduced antibody,
wherein the antibody comprises the inserted cysteine having a shielded thiol group, wherein the shielded thiol group comprises a shielding group coupled to the thiol group on the inserted cysteine,
wherein the reducing the antibody with a reducing agent comprises removing the shielding group from the shielded thiol group to provide the reduced antibody having a free thiol group on the inserted cysteine and a decoupled shielding group, and
wherein the decoupled shielding group and the reducing agent are removed through cation exchange chromatography or ultrafiltration, and oxidizing the reduced antibody to reconnect inter-chain disulfide bonds to provide an oxidized antibody,
contacting mc-vc-PAB-payload comprising a cytotoxin moiety with the oxidized antibody to conjugate the free thiol group on the inserted cysteine with the cytotoxin moiety to provide the cysteine modified antibody-cytotoxin conjugate, and
removing the unconjugated mc-vc-PAB-payload by cation exchange chromatography or ultrafiltration.

7. The cysteine modified antibody-cytotoxin conjugate of claim 1, wherein the cytotoxin and the antibody has a ratio of 1.6 to 2.

* * * * *